United States Patent
Gahali-Sass et al.

(10) Patent No.: US 11,583,573 B2
(45) Date of Patent: Feb. 21, 2023

(54) HIGH CONCENTRATED PROTEIN COMPOSITIONS FOR PREVENTING TISSUE ADHESION

(71) Applicant: Omrix Biopharmaceuticals Ltd., Rehovot (IL)

(72) Inventors: Inbar Gahali-Sass, Mazkeret Batya (IL); Israel Nur, Nes-Ziona (IL); Erez Ilan, Kibbutz Netzer Sereni (IL); Ronen Eavri, Binyamina (IL)

(73) Assignee: Omrix Biopharmaceuticals Ltd., Rehovot (IL)

( * ) Notice: Subject to any disclaimer, the term of this patent is extended or adjusted under 35 U.S.C. 154(b) by 321 days.

(21) Appl. No.: 16/710,521

(22) Filed: Dec. 11, 2019

(65) Prior Publication Data

US 2020/0188488 A1 Jun. 18, 2020

Related U.S. Application Data

(60) Provisional application No. 62/778,331, filed on Dec. 12, 2018.

(30) Foreign Application Priority Data

Dec. 12, 2018 (IL) .......................................... 263679

(51) Int. Cl.
| | |
|---|---|
| *A61K 38/46* | (2006.01) |
| *A61K 38/36* | (2006.01) |
| *A61K 38/48* | (2006.01) |
| *A61P 41/00* | (2006.01) |
| *A61K 38/37* | (2006.01) |
| *A61K 9/08* | (2006.01) |
| *A61P 7/04* | (2006.01) |
| *A61K 33/06* | (2006.01) |
| *A61K 38/38* | (2006.01) |

(52) U.S. Cl.
CPC .............. *A61K 38/363* (2013.01); *A61K 9/08* (2013.01); *A61K 33/06* (2013.01); *A61K 38/366* (2013.01); *A61K 38/37* (2013.01); *A61K 38/38* (2013.01); *A61K 38/4833* (2013.01); *A61P 7/04* (2018.01); *A61P 41/00* (2018.01); *C12Y 304/21005* (2013.01)

(58) Field of Classification Search
None
See application file for complete search history.

(56) References Cited

U.S. PATENT DOCUMENTS

| | | | |
|---|---|---|---|
| 2,390,074 A | 12/1945 | Cohn | |
| 4,297,344 A | 10/1981 | Schwinn et al. | |
| 4,455,300 A | 6/1984 | Wallace et al. | |
| 5,989,215 A * | 11/1999 | Delmotte | .............. A61L 31/046 604/82 |
| 6,121,232 A | 9/2000 | Nur et al. | |
| 6,613,325 B1 | 9/2003 | Amery et al. | |
| 6,965,014 B1 | 11/2005 | Delmotte | |
| 9,213,035 B2 * | 12/2015 | De Anglis | ................ C12Q 1/56 |
| 9,328,338 B2 | 5/2016 | Meidler et al. | |
| 2002/0001584 A1 | 1/2002 | Metzner et al. | |
| 2020/0188488 A1* | 6/2020 | Gahali-Sass | ............ A61L 31/14 |
| 2020/0188489 A1* | 6/2020 | Nur | ........................ A61K 33/06 |

FOREIGN PATENT DOCUMENTS

| | | |
|---|---|---|
| EP | 0534178 | 4/2001 |
| EP | 1837039 B1 | 8/2001 |
| EP | 1390485 | 10/2006 |
| WO | 98/033533 | 8/1998 |
| WO | 98/055140 A1 | 12/1998 |
| WO | 2013001524 A1 | 1/2013 |

OTHER PUBLICATIONS

C.W. Dunnett, Dunnett's Test New Tables for Multiple Comparisons with a Control, Biometrics, 1964, pp. 482-491, vol. 20.

Cohn, et al., A System for the Separation of the Components of Human Blood: Quantitative Procedures for the Separation of the Protein Components of Human Plasma, Separation of Protein Components of Human Plasma, Jan. 1950, pp. 465-474, vol. 72.

Cohn, et al., Preparation and Properties of Serum and Plasma Proteins. IV a System for the Separation in Fractions of the Protein and Lipoproten Components of Biological Tissues and Fluids, Journal American Chemical Society, 1945, pp. 459-475, vol. 68.

(Continued)

*Primary Examiner* — Hope A Robinson
(74) *Attorney, Agent, or Firm* — David R. Crichton

(57) ABSTRACT

Disclosed herein is an anti-adhesion kit comprised of: (i) a fibrinogen solution component comprising: fibrinogen at a concentration of about 5 to 25 mg/ml; and free calcium ions at a concentration ranging from 0.1 µM to 1 mM; and (ii) a thrombin component containing thrombin. Further disclosed is an anti-adhesion kit comprised of: (i) a fibrinogen solution component containing fibrinogen at a concentration of 8% to 25% of total protein by weight, and optionally free calcium ions at a concentration ranging from 0.1 µM to 1 mM; wherein a total protein concentration ranges from about 80 to 120 mg/ml; and (ii) a thrombin component containing thrombin. Methods of using the kits e.g., to provide anti-adhesion curable compositions are also disclosed.

5 Claims, No Drawings

(56) References Cited

OTHER PUBLICATIONS

Guerrier, et al., Specific Sorbent to Remove Solvent-Detergent Mixtures from Virus-Inactivated Biological Fluids, Journal of Chromatography, 1995, pp. 119-125, vol. 664.
Wiseman, Effect of Different Barriers of Oxidized Regenerated Cellulose (ORC) on Cecal and Sidewall Adhesions in the Presence and Absence of Bleeding, Journal of Investigative Surgery, 1999, pp. 141-146, vol. 12.
Wiseman, et al., Effect of Thrombin Induced Hemostasis on the efficacy of an Absorbable Adhesion Barrier, The Journal of Reproductive Medicine, 1992, pp. 766-770, vol. 37 Issue 9.
Wiseman, et al., The Effect of Tranexamic Acid in Fibrin Sealant on Adhesion Formation in the rat, Wiley Periodicals, Inc., Jun. 24, 2003, pp. 222-230, vol. 68B.

* cited by examiner

HIGH CONCENTRATED PROTEIN COMPOSITIONS FOR PREVENTING TISSUE ADHESION

FIELD OF THE INVENTION

The present invention relates, inter alia, to kits, compositions, and method for preventing tissue adhesion. More specifically, but not exclusively, the present invention relates to protein compositions for preventing tissue adhesion.

BACKGROUND OF THE INVENTION

One of the problems in intra-abdominal surgeries is the generation of post-operative adhesions. Such adhesions often lead to pain, discomfort, immobility and in some instances to infertility and even life-threatening bowel strangulation, which frequently necessitates a second operative procedure to remove these adhesions. The second operative procedure also bears the risk of forming adhesions. Therefore, adhesions prevention has a major medical importance.

The currently available solutions are either insufficiently efficient, require large amount of plasma source material, are laborious or have limited industrial applicability.

WO98055140 discloses a fibrinogen concentrate having a fibrinogen concentration of less than 80% of the total protein and with at least 20% of naturally occurring plasma proteins, such as fibronectin, factor VIII, von Willebrand factor, factor XIII, and vitronectin, of the total protein.

EP 1837039 discloses a fabric adhesive having stabilization in liquid or in frozen state and being stored in fibrinogen preparation, with chaotrope substance being added, where a thrombin preparation reduces or prevents the postoperative fabric adhesive diseases.

U.S. Pat. No. 6,965,014 discloses a bioerodible fibrin material which is obtained by mixing fibrinogen and thrombin reconstituted or diluted with a particular high tonic strength medium, free of calcium. Such a fibrin-based biomaterial develops a tight structure with thin fibers and small pore size suitable for use as an anti-adhesion barrier.

U.S. Pat. No. 6,613,325 discloses that a fibrin polymer film formed by applying materials most closely resembling the natural clotting materials to a surgical adhesion formation.

Wiseman D et al., The effect of tranexamic acid in fibrin sealant on adhesion formation in the rat. J. Biomed. Mater. Res. B Appl. Biomater. (2004); 68(2):222-30, describes that fibrin containing either tranexamic or aprotinin reduced the incidence and severity of adhesions.

Acknowledgement of the above references herein is not to be inferred as meaning that these are in any way relevant to the patentability of the presently disclosed subject matter.

SUMMARY OF THE INVENTION

The present invention relates, inter alia, to kits, mixtures, hydrogels, methods and compositions for preventing tissue adhesion. More specifically, but not exclusively, the present invention relates to protein-comprising kits and compositions for preventing tissue adhesion.

According to an aspect of the present invention, there is provided an anti-adhesion kit comprising at least two containers:
  (i) a first container comprising a fibrinogen solution component comprising: fibrinogen at a concentration of about 5 to 25 mg/ml; and free calcium ions at a concentration ranging from 0.1 µM to 1 mM; and
  (ii) a second container comprising a thrombin component comprising thrombin.

In some embodiments, the first container and the second container are in no direct contact in the kit. In some embodiments, the fibrinogen solution component and the thrombin component are in no direct contact in the kit.

According to another aspect of the present invention, there is provided an anti-adhesion kit comprising:
  (i) a fibrinogen solution component comprising fibrinogen at a concentration in the range of about 8% to about 25% of total protein by weight, and optionally free calcium ions at a concentration ranging from 0.1 µM to 1 mM; wherein a total protein concentration ranges from about 80 to 120 mg/ml; and
  (ii) a thrombin component comprising thrombin.

In some embodiments of any aspect of the kit, the thrombin component comprises free calcium ions.

In some embodiments of any aspect of the kit, the thrombin component is devoid of chelating agent and/or calcium precipitating agent.

In some embodiments of any aspect of the kit, the fibrinogen is present in the fibrinogen component at a concentration range of 10 to 20 mg/ml.

In some embodiments of any aspect of the kit, each of the fibrinogen component and the thrombin component is devoid of: potassium citrate, ethylenediaminetetraacetic acid (EDTA), ethylene glycol-bis(β-aminoethyl ether)-N,N,N',N'-tetra-acetic acid (EGTA), and PBS.

In some embodiments, the fibrinogen solution component comprises albumin at a concentration of at least about 20% of the total proteins by weight.

In some embodiments of any aspect of the kit, the fibrinogen solution component comprises albumin at a concentration ranging from 60 to 110 mg/ml.

In some embodiments of any aspect of the kit, the fibrinogen is originated from concentrated cryo-precipitate.

In some embodiments of any aspect of the kit, the fibrinogen is originated from concentrated viral inactivated plasma cryo-precipitate.

In some embodiments of any aspect of the kit, the fibrinogen solution component further comprises factor XIII at a concentration of at least 1 IU/ml.

In some embodiments of any aspect of the kit, the fibrinogen is present in the fibrinogen solution component at a concentration of below about 14%, of total protein by weight.

In some embodiments of any aspect of the kit, the thrombin component is in the form of a liquid solution.

In some embodiments of any aspect of the kit, the thrombin is present in the thrombin solution at a concentration ranging from 100 to 300 IU/ml.

In some embodiments of any aspect of the kit, one or both of the fibrinogen solution component and the thrombin component further comprise one or more excipients.

Excipients that may be present in the fibrinogen solution component are selected from, without being limited thereto, sodium chloride, arginine hydrochloride, glycine, and any combination thereof.

Excipients may be present in the one or more of following concentrations in the fibrinogen solution component: sodium chloride, e.g., at 120 mM, citrate 2.2-3.1 mg/ml, arginine hydrochloride 18.5-22.5 mg/ml, glycine 7-9 mg/ml, at pH of 6.7-7.2.

Excipients that may be present in the in the thrombin component are selected from, without being limited thereto, albumin, acetate, mannitol, calcium, and any combination thereof.

Excipients may be present in the following concentrations in the thrombin component: total protein 5.6-6.5 mg/ml, albumin 5-6.5 mg/ml, acetate 18-20 mM, mannitol 18.5-20.5 mg/ml, calcium 38-42 mM, at pH of 6.8-7.2.

In some embodiments of any aspect of the kit, the kit is for use in producing an anti-adhesive curable composition. In some embodiments, the composition is for use in preventing tissue adhesion following surgical procedures selected from post-operative procedures, or laparoscopic procedures, e.g., resolving intestinal obstruction, and abdominal or genecology surgery. In some embodiments, the composition is used by spraying or dripping the composition onto a site to be treated.

In some embodiments of any aspect of the kit, the kit is for use in preventing tissue adhesion.

According to another aspect of the present disclosure there is provided a mixture comprising fibrinogen, calcium and thrombin, wherein the fibrinogen is present at a concentration of 3 to 15% of a total protein by weight, the total protein concentration ranges from about 40 to about 120 mg/ml, and the thrombin is present at a concentration of about 50-150 IU/ml.

According to another aspect of the present invention, there is provided a hydrogel composition comprising fibrin, thrombin, calcium and albumin, wherein the fibrin is present at a concentration range of about 3 to about 15% of a total protein by weight, the thrombin is present at a concentration range of about 50 to about 150 IU/ml, and the albumin is present at a concentration of at least about 60% of total protein by weight.

According to another aspect of the present invention, there is provided a hydrogel composition comprising fibrin, thrombin, and calcium, wherein the fibrin is present at a concentration range of about 3 to 15% of a total protein by weight, and the thrombin is present at a concentration range of about 50 to 150 IU/ml.

According to another aspect of the present invention, there is provided a hydrogel composition comprising fibrin, calcium and thrombin, wherein the fibrin is present at a concentration range of about 4 to 12.5% of a total protein by weight, the total protein concentration ranges from about 80 to about 120 mg/ml, and the thrombin is present at a concentration range of about 50-150 IU/ml.

According to another aspect of the present invention, there is provided a hydrogel composition comprising: calcium, ranging about 5-10 mg/ml fibrin, about 50-150 IU/ml thrombin, and optionally further comprising a range of about 15-60 mg/ml albumin.

According to another aspect of the present invention, there is provided a hydrogel composition comprising: calcium, ranging about 40-65 mg/ml total protein, a range of about 5-10 mg/ml fibrin, a range of about 50-150 IU/ml thrombin, and optionally further comprising a range of about 15-60 mg/ml albumin.

In some embodiments of any aspect of the hydrogel composition, the calcium is present at a concentration range of about 0.05 µM to 40 mM, or 0.1 µM to 25 mM.

In some embodiments of any aspect of the hydrogel composition, the hydrogel composition provided herein is characterized in that it retains less than 80%, of its initial liquid (e.g., water) content under ambient conditions. For example, retains less than 70%, less than 60%, less than 50%, less than 40%, or less than 30% of the water content of the hydrogel by weight under ambient conditions. In some embodiments the hydrogel composition retains water content in the range of 35.0% to 65% by weight under ambient conditions. In an exemplary embodiment, the hydrogel retains a water content in the range 37.4%-61.6% by weight under ambient conditions. By "retains water content under ambient conditions" or any grammatical inflection thereof, it is meant to refer to water content as measured after about 1 or 2 hours at room temperature and about 1-2 atmosphere (atm) following hydrogel formation.

In one embodiment the initial liquid content is at least 85% by weight. For example, an initial water content of the hydrogel composition is in the range of 85% to 95% for example 85, 87, 88, 89, 90, 91, 92, 93, 94 or 95% by weight including any value and range therebetween. In one embodiment ambient pressure is equal to or less than 2 atm, such as 0.1 to 2 atm, e.g., 0.1, 0.2, 0.3, 0.4, 0.5, 0.6, 0.7, 0.8, 0.9, 1, 1.2, 1.3, 1.4, 1.5, 1.6, 1.7, 1.8, 1.9, or 2 atm, including any value and range therebetween.

Without being bound by any particular mechanism, it may be assumed that the structure of the disclosed hydrogel allows to release therefrom water content as a function of time under ambient conditions. As exemplified in the Example 4 below, the hydrogel releases a water content in the range of 38.4/6-62.6% by weight after 1 or 2 hours from hydrogel formation.

In some embodiments of any aspect of the hydrogel composition, wherein the hydrogel composition comprises albumin, e.g., about 15-60 mg/ml albumin, the hydrogel composition is characterized in that it retains less than 80%, less than 75%, less than 70%, less than 65%, less than 60%, less than 55%, or less than 50% of its initial liquid (e.g., water) content upon applying on a surface thereof a pressure equal to or more than 25 atm, such as 28 to 32 atm. e.g., 28, 29, 30, 31, or 32 atm (or in a range of 400 to 500 PSI), including any value and range therebetween for a time duration of about 30 minutes.

In some embodiments of any aspect of the hydrogel composition, wherein the hydrogel composition comprises albumin, e.g., about 15-60 mg/ml albumin, the hydrogel composition is characterized in that it retains initial liquid content (e.g., water) in a range of about 20 to 80%, 25 to 75%, or 20 to 60%, upon applying on a surface thereof a pressure equal to or more than 25 atm, such as 28 to 32 atm, e.g., 28, 29, 30, 31, or 32 atm, including any value and range therebetween for a time duration of about 30 minutes.

In some embodiments, albumin is present in the hydrogel at a high concentration such as in the range of about 45-52 mg/ml, and at a fibrinogen component diluted about 1:4 (in Table 9 Exp 1, and 5) water retention is in the range of about 50% to 65% of the initial weight, upon applying on a surface thereof a pressure equal to or more than 25 atm, such as 28 to 32 atm, e.g., 28, 29, 30, 31, or 32 atm, including any value and range therebetween for a time duration of about 30 minutes.

In some embodiments the total protein concentration is high e.g. of about 50 mg/ml (or 35 to 60 mg/ml) at a fibrinogen dilution of 1:4 (in Table 9 Exp 1, and 5) water retention in the range of about 50% to 65% of the initial weight, upon applying on a surface thereof a pressure equal to or more than 25 atm, such as 28 to 32 atm. e.g., 28, 29, 30, 31, or 32 atm, including any value and range therebetween for a time duration of about 30 minutes.

In some embodiments, albumin is present in the hydrogel at a high concentration such as in the range of about 45-52 mg/ml, and at a fibrinogen component diluted about 1:8 (in Table 9 Exp 2, 6 and 10) the range of water retention decreases to about 29% to about 7% of the initial weight, upon applying on a surface thereof a pressure equal to or more than 25 atm, such as 28 to 32 atm, e.g., 28, 29, 30, 31, or 32 atm, including any value and range therebetween for a time duration of about 30 minutes.

In some embodiments the total protein concentration is when the total protein is about 50 mg/ml (or 35 to 60 mg/ml), and dilution of fibrinogen component of 1:8 (in Table 9 Exp 2, 6 and 10) the range of water retention decreases to about 29% to about 7% of the initial weight, upon applying on a surface thereof a pressure equal to or more than 25 atm, such as 28 to 32 atm, e.g., 28, 29, 30, 31, or 32 atm, including any value and range therebetween for a time duration of about 30 minutes.

Water retention of the hydrogel is minimal (about 7%) under conditions of fibrinogen component diluted about 1:8 (70 mg/ml:9=7.7 mg/ml) albumin concentration of about 50% and complete depletion of calcium ions (Table X sample 10 when even the thrombin component TH03 lacks calcium), upon applying on a surface thereof a pressure equal to or more than 25 atm, such as 28 to 32 atm, e.g., 28, 29, 30, 31, or 32 atm. including any value and range therebetween for a time duration of about 30 minutes.

The need of a hydrogel being capable of retaining a liquid or not may depend, for example, on the desired therapeutic use of the hydrogel, the desired structure of the hydrogel, or the desired organ to be applied.

Without being bound by any particular theory or mechanism, it may be assumed that a capability of the hydrogel composition to release liquid (e.g., water, release of at least 70% from initial amount of liquid upon applying high pressure such as 400-500 PSI) therefrom allows to generate more compressed fiber network of the anti-adhesive composition. That is, for example in a condition in which a high pressure is applied on the disclosed composition, e.g., by a bodily organ, such as peristaltic organ, the composition may form a small thickness film, thereby reducing the likelihood of stimulating an immune system response and/or interfering with the normal action of the organ, and at the same time, increasing the biodegradation rate of the composition.

The greater degree of water retention such as more than about 50% e.g. in the range of about 50% to 65% (e.g. upon applying a high pressure such as 400-500 PSI) is indicative of the strong structure of the gel or barrier. Such a gel is capable to retain water despite being subjected to high pressure, compression, or impact stress e.g. by a neighboring tissue.

Also, a greater degree of water retention (such as about 50% or more e.g. in the range of about 50% to 65%; e.g. upon applying a high pressure such as 400-500 PSI) is particularly beneficial to the therapeutic use of the hydrogel. The retention of water may be necessary for the control of the concentration of therapeutic agents if contained within the fibrin hydrogel, as well as for the effective release of these therapeutic agents and additives. The ability of fibrin hydrogels to retain water while being subjected to compression forces was tested and compared to the water retaining capacity of a classic fibrin material. In particular, compression was applied by centrifugation of the materials at various rotational speeds and the amount of water retained was measured. A refrigerated centrifuge (Sorvall RT 6000B) spun fibrin hydrogels at different speeds:

In some embodiments, the hydrogel is characterized in that it retains at less than 80%, the initial water content upon applying on a surface thereof a high pressure ranging from 400 to 500 PSI or 28 to 35 atm. for about 30 minutes.

According to another aspect of the present invention, there is provided a method of preparing an anti-adhesive curable composition comprising the step of:

combining: (i) a fibrinogen solution component comprising: fibrinogen at a concentration range of 8 to 25% of a total protein by weight, and optionally calcium at a concentration ranging from 0.1 µM to 1 mM, wherein the total protein concentration ranges from about 80 to 120 mg/ml; and (ii) a thrombin component comprising thrombin, thereby obtaining the anti-adhesion curable composition.

According to another aspect of the present invention, there is provided a method of preparing an anti-adhesive curable composition comprising the step of:

combining: (i) a fibrinogen solution component comprising calcium at a concentration ranging from 0.1 µM to 1 mM; and fibrinogen at a concentration of about 5 to 25 mg/ml; and (ii) a thrombin component comprising thrombin, thereby obtaining the anti-adhesion curable composition.

The aspects of preparing an anti-adhesive curable composition as disclosed herein are also referred to as: "the preparation method".

In some embodiments of any aspect of the preparation method, the thrombin is present in a liquid solution at a concentration of 100 to 300 IU/ml.

In some embodiments of any aspect of the preparation method, the fibrinogen solution component and the thrombin solution are combined in a ratio (v/v) of 1:1.2 to 1.2:1 thereof.

In some embodiments, the curable composition comprises: fibrinogen, fibrin, or their combination, at a concentration range of about 3 to 15%, or 4 to 13% of the total protein, and thrombin at a concentration range of 50 to 150 IU/ml.

In some embodiments of any aspect of the preparation method, the thrombin is in the form of a powder.

In another aspect, there is provided a cured hydrogel formed by the preparation method according to any aspect or embodiments thereof.

According to another aspect of the present invention, there is provided a method for preventing tissue adhesion comprising the steps of:

(i) providing a fibrinogen solution component comprising: and fibrinogen at a concentration range of 8 to 25% of total protein by weight, and optionally free calcium ions at a concentration ranging from 0.1 µM to 1 mM; wherein a total protein concentration ranges from about 80 to 120 mg/ml;

(ii) providing a thrombin component comprising thrombin; and (iii) simultaneously spraying or dripping the fibrinogen solution component and the thrombin component onto a desired location of the tissue.

According to another aspect of the present invention, there is provided a method for preventing tissue adhesion comprising the steps of:

(i) providing a fibrinogen solution component comprising: free calcium ions a concentration ranging from 0.1 µM to 1 mM; and fibrinogen at a concentration of about 5 to 25 mg/ml;

(ii) providing a thrombin component comprising thrombin;

(iii) simultaneously spraying or dripping the fibrinogen solution component and the thrombin component onto a desired location of the tissue.

The aspects of the method for preventing tissue adhesion as disclosed herein are also referred to as: "the tissue adhesion prevention method".

In some embodiments of any aspect of the tissue adhesion prevention method, the thrombin is present in a liquid solution at a concentration of 100 to 300 IU/ml.

In some embodiments of any aspect of the tissue adhesion prevention method and the preparation method, the fibrinogen solution further comprises albumin at a concentration ranging from 60 to 110 mg/ml.

In some embodiments of any aspect of the tissue adhesion prevention method and the preparation method, the fibrinogen in the fibrinogen component is present at a concentration of 10 to 20 mg/ml.

In some embodiments, the fibrinogen solution component comprises albumin at a concentration of at least 15% of the total proteins by weight.

In some embodiments of any aspect of the tissue adhesion prevention method and the preparation method, the thrombin component comprises free calcium ions.

In some embodiments of any aspect of the tissue adhesion prevention method and the preparation method, the thrombin component is devoid of chelating agent.

In some embodiments of any aspect of the tissue adhesion prevention method and the preparation method, each of the fibrinogen component and the thrombin component is devoid of: potassium citrate, ethylenediaminetetraacetic acid (EDTA), ethylene glycol-bis(β-aminoethyl ether)-N,N,N',N'-tetra-acetic acid (EGTA), and phosphate buffered saline (PBS).

In some embodiments of any aspect of the tissue adhesion prevention method and the preparation method, the fibrinogen solution component comprises albumin at a concentration ranging from 60 to 110 mg/ml.

In some embodiments of any aspect of the tissue adhesion prevention method and the preparation method, the fibrinogen is originated from concentrated cryo-precipitate.

In some embodiments of any aspect of the tissue adhesion prevention method and the preparation method, the fibrinogen is originated from concentrated viral inactivated plasma cryo-precipitate.

In some embodiments of any aspect of the tissue adhesion prevention method and the preparation method, the fibrinogen solution component further comprises factor XIII at a concentration of at least 1 IU/ml.

In some embodiments of an aspect of the tissue adhesion prevention method or the preparation method, the fibrinogen is present in the fibrinogen solution component at a concentration of below 14%, of total protein, by weight.

In some embodiments of any aspect of the tissue adhesion prevention method and the preparation method, the thrombin component is in the form of a liquid solution.

In some embodiments of an aspect of the tissue adhesion prevention method or the preparation method, the thrombin is present in the thrombin solution at a concentration ranging from 100 to 300 IU/ml.

In some embodiments of any aspect of the tissue adhesion prevention method and the preparation method, one or both of the fibrinogen solution component and the thrombin component further comprise one or more excipients as described hereinabove.

According to another aspect, there is provided a two-component composition comprising: component A comprising a fibrinogen solution comprising a fibrinogen at a concentration range of 8% to 25% of total protein by weight, and optionally free calcium ions at a concentration ranging from 0.1 µM to 1 mM; wherein a total protein concentration ranges from about 80 to 120 mg/ml; and component B comprising a thrombin component. In some embodiments, combination of component B with component A gives rise to an anti-adhesive curable mixture.

In some embodiments, the mixture is obtained by combining ex vivo the fibrinogen-containing solution and the thrombin.

According to another aspect, there is provided a two-component composition comprising: component A comprising a fibrinogen solution comprising fibrinogen at a concentration of about 5 to 25 mg/ml; and free calcium ions at a concentration ranging from 0.1 µM to 1 mM; and component B comprising a thrombin component. In some embodiments, combination of component B with component A gives rise to an anti-adhesive curable mixture.

In some embodiments, the mixture is obtained by combining ex vivo the fibrinogen-containing solution and the thrombin.

In some embodiments of any aspect of the two-component composition, the thrombin component comprises calcium ions, e.g., free calcium ions. e.g., at a concentration of 0.1 µM to 42 Mm.

In some embodiments of any aspect of the two-component composition, the thrombin component is devoid of chelating agent.

In some embodiments of any aspect of the two-component composition, the fibrinogen in the fibrinogen component is present at a concentration of 10 to 20 mg/ml.

In some embodiments of any aspect of the two-component composition, the thrombin component is in the form of a liquid solution.

In some embodiments of any aspect of the two-component composition, the thrombin is present in the thrombin solution at a concentration ranging from 100 to 300 IU/ml.

In some embodiments of any aspect of the two-component composition, the component A and the component B are present at a ratio ranging from 1.2:1 to 1:1.2, by volume.

In exemplary embodiments of any aspect of the kit, two-component composition, or method provided herein, the fibrinogen component comprises fibrinogen, human albumin, sodium chloride, citrate, arginine hydrochloride, and glycine.

In exemplary embodiments of any aspect of the kit, two-component composition, or method provided herein, the fibrinogen component comprises fibrinogen at a concentration of 10-20 mg/ml, human albumin at a concentration of 60-110 mg/ml, sodium chloride e.g., at a concentration of 120 mM, Citrate at a concentration of 2.2-3.1 mg/ml, Arginine hydrochloride at a concentration of 18.5-22.5 mg/ml, and glycine at a concentration of 7.0-9.0 mg/ml. In exemplary embodiments, the fibrinogen component comprises total protein at a concentration of 80-120 mg/ml.

The kit according with the present invention comprise two components, being separated one from the other. In other words, each one of the two components is confined in a separated container. In some embodiments, the fibrinogen-containing component and/or the thrombin-containing component may be in the form of an applicator. In some embodiments, the applicator comprises a barrel holding the fibrinogen-containing component and/or the thrombin-containing component disclosed herein and a re-sealable opening for delivery therethrough of the fibrinogen-containing component and/or the thrombin-containing component.

In some embodiments, the applicator is a syringe. Application may be by pushing each one of the components out of the syringes and mixed to form a composition to be directly applied to a desired target site. The fibrinogen-containing component and/or the thrombin-containing component may be in liquid form, in a lyophilized form or in dry form, the latter is to be wetted (e.g. with saline) prior to application. In some embodiments, the fibrinogen-containing component and/or the thrombin-containing component may be applied at a tissue to be treated used by, for example, spraying or dripping.

The applicator can be for single use, i.e. to be disposed after all or a portion of the fibrinogen-containing component and/or the thrombin-containing component is used: or it may be designed for multiple uses such that the applicator's opening is resealed between uses.

Once fibrinogen and thrombin are brought into contact with each other, e.g., on a tissue, clotting initiates and fibrin clot-based tissue adhesive is formed. Thus, application of fibrinogen-containing component and the thrombin-containing component results in formation of a sealant formulation. In the context of the present invention, the term "sealant formulation" is to be understood as a tissue adhesive, the formulation having ingredients that upon contact with each other, e.g. on a tissue, or blood react to subsequently form into a tissue adhesive formulation. Thus, the present disclosure relates in some aspects to a two-component composition for use in preventing tissue adhesion, comprising a first component (component A) comprising a fibrinogen-containing solution comprising a fibrinogen at a concentration range of between about 5 mg/ml to about 30 mg/ml and a total protein concentration range is between about 80 mg/ml to about 120 mg/ml and a second component (component B) comprising a thrombin.

Application of the fibrinogen-containing component and the thrombin-containing composition on a target tissue (either by mixing a-priori or not) results in formation of a gel having an increased viscosity as compared to each one of the individual components.

According to another aspect of the present invention, there is provided a method for preventing tissue adhesion comprising applying the two-component composition on at least one surface or area of the tissue.

In exemplary embodiments of any kit, two-component composition, or method provided herein, the thrombin component comprises thrombin, human albumin, acetate, mannitol, and calcium.

In exemplary embodiments of any kit, two-component curable composition, or method provided herein, the thrombin component comprises thrombin at a concentration of 100 to 300 IU/ml, human albumin at a concentration of 5.0-6.5 mg/ml, acetate at a concentration of 18-20 mM, mannitol at a concentration of 18.5-20.5 mg/ml, and calcium at a concentration of 38-42 mM. In exemplary embodiments, the thrombin component comprises total protein at a concentration of 5 to 6.5 mg/ml.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

DESCRIPTION OF EMBODIMENTS OF THE INVENTION

The present invention is based on the unexpected finding that combining thrombin and fibrinogen at their specific concentration provide a composition having anti-adhesive properties.

It was found that a fibrinogen component comprising total protein at a concentration of at least about 70 mg/ml (such as comprising about 70 to about 120 mg/ml total protein) and a low concentration of fibrinogen of about 7.7 mg/ml and less than about 17 mg/ml; such as in a range of about 9 to about 14 mg/ml; for example: about 9 mg/ml, 12 mg/ml and 14 mg/ml; can be used in a kit for efficient prevention or reduction of adhesion. It was found that using this fibrinogen component in a kit, together with a thrombin component, can form a hydrogel capable of retaining about 50% or more of initial water (e.g. in the range of about 50% to 65%) when said hydrogel is subjected to a high pressure (e.g. in the range of 400-500 PSI).

It was found that a mixture of fibrinogen and thrombin comprising total protein at a concentration of at least about 35 mg/ml (such as comprising about 50 mg/ml or in the range of about 35 to 60 mg/ml total protein) and a concentration of fibrinogen in the range of more than about 3.8 mg/ml and less than about 8.5 mg/ml such as in the range of about 4.5 to about 7 mg/ml; for example: about 4.5 mg/ml, about 6 mg/ml, and about 7 mg/ml can be used for efficient prevention or reduction of adhesion. It was found that this mixture can form a hydrogel capable of retaining about 50% of initial water or more (e.g. in the range of about 50% to 65%) when said hydrogel is subjected to a high pressure (e.g. in the range of 400-500 PSI).

It was found that a fibrinogen component comprising albumin at a concentration of at least about 60 mg/ml (such as comprising about 70 to about 120 mg/ml albumin) and a low concentration of fibrinogen of about 7.7 mg/ml to less than about 17 mg/ml such as in the range of about 9 to about 14 mg/ml; for example: 9 mg/ml, 12 mg/ml and 14 mg/ml can be used in a kit for efficient prevention or reduction of adhesion. It was found that using this fibrinogen component in a kit can, together with a thrombin component, form a hydrogel capable of retaining about 50% of initial water or more (e.g. in the range of about 50% to 65%) when said hydrogel is subjected to a high pressure (e.g. in the range of 400-500 PSI).

It was found that a mixture of fibrinogen and thrombin comprising albumin at a concentration of at least about 30 mg/ml (such as comprising about 35 to about 55 mg/ml albumin) and a low concentration of fibrinogen more than about 3.8 mg/ml and less than about 8.5 mg/ml such as such as in the range of about 4.5 to about 7 mg/ml; for example: about 4.5 mg/ml, about 6 mg/ml and about 7 mg/ml can be used for efficient prevention or reduction of adhesion. It was found that this mixture can form a hydrogel capable of retaining about 50% of initial water or more (e.g. in the range of about 50% to 65%) when said hydrogel is subjected to a high pressure (e.g. in the range of 400-500 PSI).

It was found that a fibrinogen component solution comprising albumin at a concentration of equal or more than 20% by weight (such as a range of 20 to 100% by weight) out of the total protein in the solution (such as total protein of 70 to 120 mg/ml) and a low concentration of fibrinogen of more than 7.7 mg/ml or less than 17 mg/ml such as in a range of about 9 to about 14 mg/ml; for example: about 9 mg/ml, about 12 mg/ml and about 14 mg/ml can be used in a kit for efficient prevention or reduction of adhesion. It was found that using this fibrinogen component in a kit can, together with a thrombin component, form a hydrogel capable of retaining about 50% of initial water or more (e.g. in the range of about 50% to 65%) when said hydrogel is subjected to a high pressure (e.g. in the range of 400-500 PSI).

It was found that a mixture of fibrinogen and thrombin comprising albumin at a concentration of equal or more than about 20% by weight (such as a range of about 20 to about 100% by weight) out of the total protein in the mixture (such as total protein comprising about 50 mg/ml or 35 to 60 mg/ml) and a low concentration of fibrinogen of more than about 3.8 mg/ml or less than about 8.5 mg/ml such as such as in the range of about 4.5 to about 7 mg/ml, for example: about 4.5 mg/ml, about 6 mg/ml and about 7 mg/ml can be used for efficient prevention or reduction of adhesion. It was found that this mixture can form a hydrogel capable of retaining about 50% of initial water or more (e.g. in the range of about 50% to 65%) when said hydrogel is subjected to a high pressure (e.g. in the range of 400-500 PSI).

The currently available solutions are either insufficiently efficient, require large amount of plasma source material, are laborious or have limited industrial applicability.

An object of the present invention is to provide an anti-adhesive composition which may easily be applied onto a target site of need, wherein the composition is sufficiently efficient, and requires a low amount of plasma source or raw material.

As provided hereinbelow, the inventors used the combined components of fibrinogen solution, and the thrombin to provide an anti-adhesion composition.

Surprisingly, as further demonstrated in the Examples section, combining the above-mentioned components (fibrinogen solution with the thrombin at specified concentration thereof) provided a composition characterized by anti-adhesive properties.

According to one aspect, the present application provides a two-component anti-adhesive kit comprising: a fibrinogen solution component comprising fibrinogen at a concentration of about 5 to 35 mg/ml; and a thrombin component comprising thrombin (e.g., 100-300 IU/ml). In some embodiments, combining the two components gives rise to an anti-adhesive curable composition, e.g., for use in preventing tissue adhesion. In some embodiments, one or both of the fibrinogen solution component and the thrombin component further comprise calcium.

In some such embodiments, the fibrinogen solution component comprises fibrinogen at a concentration of about 10 to 35 mg/ml. In some such embodiments, the fibrinogen solution component comprises fibrinogen at a concentration of about 10 to 30 mg/ml. In some such embodiments, the fibrinogen solution component comprises fibrinogen at a concentration of about 5, 10, 15, 20, 25, 30, or 35 mg/ml, including any value and range therebetween. In some embodiments, the total concentration of fibrinogen in the fibrinogen solution component is between 10 and 25 mg/ml. In some embodiments, the total concentration of fibrinogen in the fibrinogen solution component is between 10 and 20 mg/ml. In some embodiments, the total concentration of fibrinogen in the fibrinogen solution component is between 5 and 10 mg/ml.

In some embodiments, the fibrinogen solution component comprises fibrinogen at a concentration of 7, 8, 9, 10, 11, 12, 13, 14, 15, 16, or 17 including any value and range therebetween.

In another aspect, the present invention provides a two-component anti-adhesive kit comprising: (i) a fibrinogen solution component comprising fibrinogen at a concentration range of about 8 to 30%, or of about 8 to 25% of total protein by weight, with a total protein concentration being in a range of about 50 to 150, 60 to 140, or 80 to 120 mg/ml; and (ii) a thrombin component comprising thrombin. In some embodiments of this aspect, one or both of the fibrinogen solution component and the thrombin component further comprise calcium.

In some such embodiments, the fibrinogen is present in the fibrinogen component at a concentration range of 8% to 25% of total protein by weight. In further such embodiments, the fibrinogen is present at a concentration range of 14% to 25% of total protein by weight. In further such embodiments, the fibrinogen is present at a concentration range of 8% to 25% of total protein by weight. In further such embodiments, the fibrinogen is present at a concentration range of 9% to 14% of total protein by weight.

In some such embodiments, the fibrinogen is present in the fibrinogen component at a concentration of 8%, 9%, 10%, 11%, 12%, 13%, 14%, 15%. 16%. 17%. 18%. 19%. 20%, 21%, 22%. 23%, 24%, or 25%, including any value and range therebetween.

In some such embodiments, the fibrinogen is present in the fibrinogen component at a concentration 9%. 10%, 11%, 12%, 13%, 14% including any value and range therebetween.

In some embodiments, the total protein concentration ranges from about 80 to 120 mg/ml. In some such embodiments, the total protein concentration is e.g., 80, 85, 90, 95, 100, 105, 110, 115, or 120 mg/ml, including any value and range therebetween. In some embodiments, the total protein concentration in the fibrinogen component is about 50, 60, 70, 80, 90, 100, 110, 120, 130, 140, or 150 mg/ml, including any value and range therebetween.

Accordingly, in some embodiments, the fibrinogen component and/or the thrombin component further comprise calcium.

In some embodiments of any aspect provided herein, the fibrinogen solution component comprises calcium. In some embodiments of any aspect provided herein, the fibrinogen solution component comprises calcium at a concentration of at least 0.05 µM. In some embodiments of any aspect provided herein, the fibrinogen solution component comprises calcium at a concentration of at least 0.1 µM.

In some embodiments of any aspect provided herein, the fibrinogen solution component comprises calcium at a concentration ranging from 0.05 µM to 5 mM. In some embodiments of any aspect provided herein, the fibrinogen solution component comprises calcium at a concentration ranging from 0.075 µM to 2 mM. In some embodiments of any aspect provided herein, the fibrinogen solution component comprises calcium at a concentration ranging from 0.1 µM to 1 mM. In some embodiments of any aspect provided herein, the fibrinogen solution component comprises calcium at a concentration ranging from 0.05 µM to 1 mM. In some embodiments of any aspect provided herein, the fibrinogen solution component comprises calcium at a concentration of 0.05, 0.1, 10, 50, 100, 200, 500, or 1000 µM, including any value and range therebetween.

In some embodiments of any aspect, the thrombin component comprises calcium. In some embodiments of any aspect, the thrombin component comprises calcium at a concentration of 35 to 45 mM. In some embodiments of any aspect, the thrombin component comprises calcium. In some embodiments of any aspect, the thrombin component comprises calcium at a concentration of 38 to 42 mM.

In some embodiments of any aspect, both of the fibrinogen solution component and the thrombin component comprise calcium. Embodiments of the calcium are described hereinbelow.

Calcium may be present in, or be originated from, one or more calcium salts including, without being limited thereto, calcium chloride, calcium acetate, calcium lactate, calcium oxalate, calcium carbonate, calcium gluconate, calcium phosphate, calcium glycerophosphate, or any combination thereof. In some embodiments, the calcium salt is calcium chloride. In some embodiments, the calcium cation is originated from calcium chloride. i.e. the formulation is prepared with calcium chloride.

In some embodiments of any aspect, the calcium is non-chelated calcium.

By the term "calcium" it is also meant to encompass a plurality of calcium species (e.g., calcium cation). In some embodiments, the calcium is in the form of ion (cation). In some embodiments, the calcium is in the form of free ions.

The term "free ions" refers to ions that may be present in a dissolved form and can freely migrate through the component, mixture, the composition or the formulation. The "free ions" include ions that are not bound, or are loosely bound in a solution. In some embodiments, the free ions are non-chelated ions, or more specifically, non-chelated calcium ions.

By "non-chelated calcium" it means that at least at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or even 100% of a plurality of the calcium species (e.g., ions) are not chelated.

As used herein, the terms "chelated" or "chelation" in the context of non-chelated calcium refer to the formation or presence of one or more bonds, or other attractive interactions, between two or more binding sites within a chelating agent and a calcium species.

The term "chelating agent" as used herein is also meant to encompass calcium precipitation agent. In some embodiments, the precipitation agent generates insoluble salt of calcium ions. In exemplary embodiments, by "non-chelated calcium" it is meant to refer to calcium ions which are present in a medium devoid of precipitation agents, such as PBS.

Accordingly, in some embodiments of any aspect provided herein, wherein the fibrinogen component comprises chelating agent, at least portion of the calcium ions remain active, i.e. non-chelated. In some embodiments, "at least portion of the calcium ions" refers to at least 1 μM calcium ions. In some embodiments, "at least portion of the calcium ions" refers to 1 μM to 45 mM calcium ions.

Accordingly, in some embodiments of any aspect provided herein, the fibrinogen component, the thrombin component, or a combination thereof, comprise less than 50% (mol %) of chelating agent, by total mole of the calcium and chelating agent. In some embodiments of any aspect provided herein, the fibrinogen component comprises less than 50% (mol %) of chelating agent, by total mole of the calcium and chelating agent. In some embodiments of any aspect provided herein the thrombin component comprises less than 50% (mol %) of chelating agent, by total mole of the calcium and chelating agent.

By "less than 50% (mol %) of chelating agent" it is also meant, in some embodiments, to less than 49% (mol %) of chelating agent, less than 45% (mol %) of chelating agent, less than 40% (mol %) of chelating agent, less than 35% (mol %) of chelating agent, less than 30% (mol %) of chelating agent, less than 25% (mol %) of chelating agent, less than 20% (mol %) of chelating agent, less than 15% (mol %) of chelating agent, less than 10% (mol %) of chelating agent, or less than 5% (mol %) of chelating agent, by total mole of the calcium and chelating agent.

In some embodiments of any aspect, the thrombin is substantially devoid of chelating agent. In some embodiments of any aspect, the thrombin is substantially devoid of chelating selected from sodium citrate, potassium citrate, Ethylenediaminetetraacetic acid (EDTA), ethylene glycol-bis(D-aminoethyl ether)-N,N,N',N'-tetra-acetic acid (EGTA), poly(acrylic acid), maleic acid or an oligomer thereof, chloride solutions, phosphate solutions, or other ions in solutions having a strong affinity to calcium.

Non-limiting exemplary phosphate solution is phosphate buffered saline (PBS), e.g., in its physiologically acceptable levels. In some embodiments of any aspect, the thrombin and/or fibrinogen components are devoid of PBS.

By "substantially devoid of chelating agent" it is meant that the chelating agent may be present at a concentration of up to than 10 ppm, or, in some embodiments, the chelating agent is completely absent.

In some embodiments, one or more components from the fibrinogen solution component and the thrombin component further comprise one or more excipients selected from sodium chloride, citrate, acetate, mannitol, arginine hydrochloride, and glycine.

Excipients may be present in the following concentrations in the fibrinogen solution component: sodium chloride, e.g., 120 mM, citrate 2.2-3.1 mg/ml, arginine hydrochloride 18.5-22.5 mg/ml, glycine 7-9 mg/ml, at pH of 6.7-7.2.

Additionally or alternatively, excipients may be present in the following concentrations in the thrombin component: total protein 5.6-6.5 mg/ml, thrombin <300 IU/ml, albumin 5-6.5 mg/ml, acetate 18-20 mM, mannitol 18.5-20.5 mg/ml, calcium 38-42 mM, at pH of 6.8-7.2.

In one embodiment of the invention it is disclosed a fibrinogen component comprising total protein at a concentration of at least 70 mg/ml (such as comprising 70 to 120 mg/ml total protein) and a low concentration of fibrinogen of more than 7.7 mg/ml and less than 17 mg/ml; such as in a range of 9 to 14 mg/ml; for example: 9 mg/ml, 12 mg/ml and 14 mg/ml; can be used in a kit for efficient prevention or reduction of adhesion. Using this fibrinogen component in a kit, together with a thrombin component, can form a hydrogel capable of retaining about 50% of initial water or more (e.g. in the range of about 50% to 65%) when said hydrogel is subjected to a high pressure (e.g. in the range of 400-500 PSI). This hydrogel can be used for efficient prevention or reduction of adhesion.

In one embodiment of the invention it is disclosed a fibrinogen component comprising albumin at a concentration of at least about 60 mg/ml (such as comprising about 70 to about 120 mg/ml albumin) and a concentration of fibrinogen of about 7.7 mg/ml to less than about 17 mg/ml such as in the range of about 9 to about 14 mg/ml; for example: 9 mg/ml, 12 mg/ml and 14 mg/ml can be used in a kit for efficient prevention or reduction of adhesion. It was found that using this fibrinogen component in a kit can, together with a thrombin component, form a hydrogel capable of retaining about 50% of initial water or more (e.g. in the range of about 50% to 65%) when said hydrogel is subjected to a high pressure (e.g. in the range of 400-500 PSI).

In one embodiment of the invention it is disclosed a fibrinogen component solution comprising albumin at a concentration of equal or more than 20% by weight (such as a range of about 20 to 100% by weight) out of the total protein in the solution (such as total protein in the range of about 70 to 120 mg/ml) and a concentration of fibrinogen in the range of more than about 7.7 mg/ml and less than about 17 mg/ml such as in a range of about 9 to about 14 mg/ml; for example: about 9 mg/ml, about 12 mg/ml and about 14 mg/ml can be used in a kit for efficient prevention or reduction of adhesion. It was found that using this fibrinogen component in a kit can, together with a thrombin component, form a hydrogel capable of retaining about 50% of initial water or more (e.g. in the range of about 50% to 65%) when said hydrogel is subjected to a high pressure (e.g. in the range of 400-500 PSI).

In one embodiment of the invention it is disclosed a fibrinogen component comprising total protein at a concentration of at least about 70 mg/ml (such as comprising protein concentration in a range of about 70 to about 120 mg/ml total protein) and a concentration of fibrinogen of more than about 7.7 mg/ml and less than about 17 mg/ml; such as in a range of about 9 to about 14 mg/ml; for example: about 9 mg/ml, about 12 mg/ml and about 14 mg/ml; and free calcium ions (e.g. at a concentration ranging from about 0.1 µM to about 1 mM). The compound can be used in a kit for efficient prevention or reduction of adhesion. Using this fibrinogen component in a kit, together with a thrombin component, can form a hydrogel capable of retaining about 50% of initial water or more (e.g. in the range of about 50% to 65%) when said hydrogel is subjected to a high pressure (e.g. in the range of about 400-500 PSI). This hydrogel can be used for efficient prevention or reduction of adhesion.

In one embodiment of the invention it is disclosed a fibrinogen component comprising albumin at a concentration of at least about 60 mg/ml (such as comprising about 70 to about 120 mg/ml albumin); a low concentration of fibrinogen of more than about 7.7 mg/ml or less than about 17 mg/ml such as: about 9 mg/ml, about 12 mg/ml and about 14 mg/ml; and free calcium ions (e.g. at a concentration ranging from about 0.1 µM to about 1 mM). The compound can be used in a kit for efficient prevention or reduction of adhesion. Using this fibrinogen component in a kit can, together with a thrombin component, form a hydrogel having a water retention e.g. of at least about 50% (e.g. in the range of about 50% to 65%) from initial weight when said hydrogel is subjected to a high pressure (e.g. in the range of about 400-500 PSI).

In one embodiment of the invention it is disclosed a fibrinogen component solution comprising albumin at a concentration of equal or more than about 20% by weight (such as in a range of about 20 to about 100% by weight) out of the total protein in the solution (such as in a range of about 70 to about 120 mg/ml total protein); a low concentration of fibrinogen in a range of more than about 7.7 mg/ml or less than about 17 mg/ml such as: about 9 mg/ml, about 12 mg/ml, and about 14 mg/ml; and free calcium ions (e.g. at a concentration ranging from about 0.1 µM to about 1 mM). The compound can be used in a kit for efficient prevention or reduction of adhesion. Using this fibrinogen component in a kit can, together with a thrombin component, form a hydrogel having a water retention, e.g. of at least about 50% from initial weight (e.g. in the range of about 50% to 65%) when said hydrogel is subjected to a high pressure (e.g. in the range of about 400-500 PSI).

In exemplary embodiments, the final concentrations in the composition provided by combining the components is about half of the values listed herein, since the components are mixed at about 1:1 ratio thereof, by volume.

In one embodiment of the invention it is disclosed a mixture of fibrinogen and thrombin comprising total protein at a concentration of at least about 35 mg/ml (such as comprising about 50 mg/ml or in the range of about 35 to 60 mg/ml total protein) and a concentration of fibrinogen in the range of more than about 3.8 mg/ml and less than about 8.5 mg/ml such as in the range of about 4.5 to about 7 mg/ml; for example: about 4.5 mg/ml, about 6 mg/ml and about 7 mg/ml can be used for efficient prevention or reduction of adhesion. This mixture can form a hydrogel capable of retaining about 50% of initial water or more (e.g. in the range of about 50% to 65%) when said hydrogel is subjected to a high pressure (e.g. in the range of 400-500 PSI). This mixture can be used for efficient prevention or reduction of adhesion.

In some embodiments, the mixture is obtained by combining ex vivo the fibrinogen-containing solution and the thrombin.

In one embodiment of the invention it is disclosed a mixture of fibrinogen and thrombin comprising albumin at a concentration of at least about 30 mg/ml (such as comprising albumin in a range of about 35 to about 55 mg/ml) and a concentration of fibrinogen in a range of more than about 3.8 mg/ml and less than about 8.5 mg/ml such as such as in the range of about 4.5 to about 7 mg/ml; for example: about 4.5 mg/ml, about 6 mg/ml and about 7 mg/ml can be used for efficient prevention or reduction of adhesion. It was found that this mixture can form a hydrogel capable of retaining about 50% of initial water or more (e.g. in the range of about 50% to 65%) when said hydrogel is subjected to a high pressure (e.g. in the range of 400-500 PSI).

In some embodiments, the mixture is obtained by combining ex vivo the fibrinogen-containing solution and the thrombin.

In one embodiment of the invention it is disclosed a mixture of fibrinogen and thrombin comprising albumin at a concentration of equal or more than about 20% by weight (such as in a range of about 20 to about 100% by weight) out of the total protein in the mixture (such as total protein comprising a range of about 50 mg/ml or 35 to 60 mg/ml) and a concentration range of fibrinogen of more than about 3.8 mg/ml and less than about 8.5 mg/ml such as such as in the range of about 4.5 to about 7 mg/ml; for example: about 4.5 mg/ml, about 6 mg/ml and about 7 mg/ml can be used for efficient prevention or reduction of adhesion. It was found that this mixture can form a hydrogel capable of retaining about 50% of initial water or more (e.g. in the range of about 50% to 65%) when said hydrogel is subjected to a high pressure (e.g. in the range of 400-500 PSI).

In some embodiments, the mixture is obtained by combining ex vivo the fibrinogen-containing solution and the thrombin.

In one embodiment of the invention it is disclosed a mixture of fibrinogen and thrombin comprising albumin at a concentration of at least about 30 mg/ml (such as comprising albumin in a range of about 35 to about 55 mg/ml) and a concentration range of fibrinogen of more than about 3.8 mg/ml and less than about 8.5 mg/ml such as such as in the range of about 4.5 to about 7 mg/ml; for example: about 4.5 mg/ml, about 6 mg/ml and about 7 mg/ml; and free calcium ions. The mixture can be used for efficient prevention or reduction of adhesion. It was found that this mixture can form a hydrogel capable of retaining about 50% of initial water or more (e.g. in the range of about 50% to 65%) when said hydrogel is subjected to a high pressure (e.g. in the range of 400-500 PSI).

In some embodiments, the mixture is obtained by combining ex vivo the fibrinogen-containing solution and the thrombin.

In one embodiment of the invention it is disclosed a mixture of fibrinogen and thrombin comprising albumin at a concentration of equal or more than about 20% by weight (such as a concentration range of about 20 to about 100% by weight) out of the total protein in the mixture (such as a concentration range of about 35 to about 60 mg/ml total protein); a low concentration range of fibrinogen higher than about 3.8 mg/ml or below about 8.5 mg/ml such as such as in the range of about 4.5 to about 7 mg/ml; for example: about 4.5 mg/ml, about 6 mg/ml, and about 7 mg/ml; and free calcium ions. The mixture may be used for efficient prevention or reduction of adhesion. This mixture can form a hydrogel having a water retention. e.g. of at least about 50% from initial weight (e.g. in the range of about 50% to 65%) when said hydrogel is subjected to a high pressure (e.g. in the range of about 400-500 PSI).

In some embodiments, the mixture is obtained by combining ex vivo the fibrinogen-containing solution and the thrombin.

In some embodiments, each component of the kit of any aspect disclosed herein is provided in a different container.

In some embodiments combining the two components of the kit provides an anti-adhesive composition. In some embodiments, the anti-adhesive composition is a curable composition.

Accordingly, in some embodiments, the anti-adhesive curable composition e.g., provided by the disclosed kit comprises calcium.

As used herein, the term "anti-adhesive" means a composition that is capable of preventing adhesion in or around the area to be prevented from adhesion such as in living bodies, organs, tissues or cells, and is thus biologically acceptable. In some embodiments, the anti-adhesive composition may be biodegradable.

The anti-adhesive effect may be exerted by applying the anti-adhesive to a target area and optionally covering adhesion areas or possible adhesion areas with the anti-adhesive to inhibit the adhesion. In some embodiments, the anti-adhesive may be applied to a target area, and the other desired area is attached thereto, which is then allowed to stand or pressed for a certain period of time.

Typically, for anti-adhesion applications at the target site, e.g., surgical site, the disclosed composition allows to provide a durable sturdy physical barrier between different organs at the surgical site.

The term "durable", in the context of anti-adhesion applications, is meant to refer to providing sturdy physical barrier as described above for a duration of at least 1 day, at least 2 days, at least 3 days, at least 4 days, at least 5 days, at least 6 days, at least 7 day, at least 8 days, at least 9 days, at least 10 day, at least 11 days, at least 12 days, at least 13 days, or at least 14 days, e.g., 1 to 14 days.

The term "combining the two components" is to be understood as any form of association/contacting the two components, including one or more from: adding, dissolving, mixing, slurrying, spraying, smearing, dipping, soaking, brushing, casting, printing, injecting, and stirring the above-mentioned components, thereby providing the anti-adhesive composition (also referred to hereinthroughout as: "the combined product", "the combined composition" or "the anti-adhesive mixture", interchangeably).

In some embodiments, the fibrinogen solution component comprises fibrinogen at a concentration of less than 26%, 25%, 24%, 23%, 22%, 21%, 20%, 19%, 18%, 17%, 16%, 15%, 14%, 13%, 12%, 11%, 10%, 9%, 8%, 7%, or less than 6% of total protein by weight. In some embodiments, the fibrinogen solution component comprises fibrinogen at a concentration of less than 10% of total protein by weight. In some embodiments, the fibrinogen solution component comprises fibrinogen at a concentration of less than 7% of total protein by weight.

In some embodiments, the fibrinogen solution component comprises fibrinogen at a concentration of at least 5% of total protein by weight. In some embodiments, the fibrinogen solution component comprises fibrinogen at a concentration of between 5% and 14%. In some embodiments the fibrinogen solution component comprises fibrinogen in a concentration of, between 5% and 26%, between 5% and 25%, between 5% and 26%, between 5% and 25%, between 5% and 24%, between 5% and 23%, between 5% and 22%, between 5% and 21%, between 5% and 20%, between 5% and 19%, between 5% and 18%, between 5% and 17%, between 5% and 16%, between 5% and 15%, between 5% and 14%, between 5% and 13%, between 5% and 12%, between 5% and 11%, between 5% and 10%, between 5% and 9%, between 5% and 8%, between 5% and 7%, or between 5% and 6%, of total protein by weight. In some embodiments the fibrinogen solution component comprises fibrinogen in a concentration (of, between about 9% and 14% of total protein by weight. In some embodiments, the fibrinogen solution component comprises fibrinogen at a concentration of 5%. 7%, 8%, 9%, 10%, 11%. 12%, 13%, 14%, 15%. 16%, 17%, 18%, 19%, 20%, 21%, 22%. 23%, 24%, or 25% by total weight of the protein, including any value and range therebetween. In some embodiments, the fibrinogen solution component comprises fibrinogen at a concentration of about 9%, 10%, 11%, 12%, 13%, or 14%, by total weight of the protein, including any value and range therebetween. As used herein and in the art, the term "fibrinogen" refers to a precursor protein of the blood clot matrix. The fibrinogen has a molecular weight of about 340,000 Daltons and consists of 3 pairs of non-identical polypeptide chains. Aα, Bβ and γ, linked together by disulfide bonds. Typically, fibrinogen has a trinodular structure: two identical D terminal globular domains and a central E globular domain connected by supercoiled α-helices.

In some embodiments the fibrinogen in the fibrinogen-containing component can be purified and isolated from plasma.

In some embodiments, the fibrinogen-containing component does not contain tranexamic acid. In some embodiments, the fibrinogen-containing component does not contain aprotinin. In some embodiments, the fibrinogen-containing component is biologically active component that does not contain tranexamic acid or aprotinin. During BAC2 preparation, plasminogen (the enzyme precursor of plasmin. which breaks down fibrinogen and fibrin) and/or plasmin is removed and therefore BAC2 does not contain tranexamic acid or aprotinin.

Accordingly, in some embodiments, the fibrinogen component is BAC2 which is depleted from plasmin(ogen) and does not comprise tranexamic acid or aprotinin.

In some embodiments, fibrinogen is purified from an aluminum hydroxide precipitate from a byproduct in the manufacture process of factor VIII (FVIII)] as disclosed in WO2013001524A1.

The BAC solution can further comprise stabilizers such as arginine, lysine and other sealant additives as known in the art. In some embodiments. BAC and preferably BAC2 is derived from plasma cryoprecipitate (in particular concentrated cryoprecipitate).

Examples of fibrinogen sources include, but are not limited to, recombinant fibrinogen, purified fibrinogen, including fibrinogen component of EVICEL® (i.e. BAC2), fibrinogen component of Tisseel (containing aprotinin, an antifibrinolytic agent).

In some embodiments, cryoprecipitated fibrinogen denotes, without being limited thereto, fresh frozen plasma precipitate following centrifugation containing total protein in the range of 30 to 6) mg/ml; total viable count (TVC) <1000 CF U/ml; Factor XIII, 2 to 9 IU/ml; Fibronectin—0.5 to 6 mg/ml; and Colttable Fibrinogen—18 to 39 mg/ml.

Fibrinogen concentrate may also be obtained commercially. Examples of fibrinogen include, but are not limited to, fibrinogen component of EVICEL® (i.e. BAC2), fibrinogen component of Tisseel (containing aprotinin, an antifibrinolytic agent).

In some embodiments, the fibrinogen-containing component is diluted BAC2. As noted above BAC2 does not include tranexamic acid or aprotinin. It was previously considered that tranexamic acid and/or aprotinin are required for reducing tissue anti-adhesion. It was surprisingly found that although the fibrinogen-containing component (i.e. diluted BAC2) does not contain tranexamic acid or aprotinin, an efficient anti-adhesion activity was observed.

In some embodiments, the fibrinogen-containing component comprises BAC2 diluted by at least a factor of two. In some embodiments, the fibrinogen-containing component comprises BAC2 diluted by a factor of between two to ten. In some embodiments, the fibrinogen-containing component comprises BAC2 diluted by a factor of three. In some embodiments, the fibrinogen-containing component comprises BAC2 diluted by a factor of four. In some embodiments, the fibrinogen-containing component comprises BAC2 diluted by a factor of eight.

A variety of buffers may be used for the dilution of fibrinogen-containing component. In some embodiments, the buffer comprises at least one of sodium chloride, tri-sodium citrate dihydrate, glycine, arginine hydrochloride and calcium chloride dihydrate. In some embodiments, the buffer comprises about 120 mM sodium chloride, about 10 mM tri-sodium citrate dihydrate, about 120 mM glycine, about 9.5 mM arginine hydrochloride and about 1 mM calcium chloride dihydrate. In some embodiments, the buffer has a pH value of 7.0-7.2. An exemplary buffer is as shown in Table 3 below.

In some embodiments, as appreciated, the amount of fibrinogen in the fibrinogen-containing component is determined by the dilution factor of BAC2. In some embodiments, the combined diluted fibrinogen-containing component and diluted thrombin-containing component comprises above 20% albumin by weight of total protein.

In some embodiments, the fibrinogen is or originated from fibrinogen concentrate. In some embodiments, the fibrinogen is a blood derived fibrinogen concentrate.

Hereinthroughout, the terms "originated from" or "derived from" are used interchangeably and refer to an origin or source of the relevant component, which may include naturally occurring, recombinant, processed, unpurified or purified molecules (e.g., the relevant protein).

In some embodiments, the fibrinogen comprises cryoprecipitated fibrinogen. In some embodiments, the fibrinogen is originated from cryoprecipitated fibrinogen.

In the context of the present disclosure, the term "cryoprecipitated fibrinogen" refers to fibrinogen obtained from frozen plasma, typically the latter prepared from whole blood.

In some embodiments, cryoprecipitate is obtained when frozen plasma thawed in the cold, typically at a temperature of 0-4° C., resulting in the formation of a precipitate that comprises predominantly the fibrinogen. In some embodiments, the cryoprecipitate is collected, for example by centrifugation and is then dissolved in a suitable buffer such as a buffer containing 120 mM sodium chloride, 10 mM trisodium citrate, 120 mM glycine, or 95 mM arginine hydrochloride.

In some embodiments, the fibrinogen solution comprises one or more additional factors selected from, without being limited thereto, factor XIII, factor VIII, fibronectin, von Willebrand factor (vWF), and vitronectin.

In some embodiments, the cryoprecipitated fibrinogen is regarded as the biologically active component (BAC) of blood plasma. In some embodiments, the BAC is viral inactivated.

In some embodiments, BAC is a biologically active component that comprises an antifibrinolytic agent such as, without being limited thereto, tranexamic acid.

This is considered as a second-generation BAC and is referred to in the art as BAC2. During BAC2 preparation, plasminogen (the enzyme precursor of plasmin, which breaks down fibrinogen and fibrin) is removed.

Non-limiting preparation routes of BAC are described in U.S. Pat. No. 6,121,232 and/or WO98/033533 the contents of which is incorporated by reference.

In some embodiments, a BAC composition comprises one or more anti-fibrinolytic agents (e.g., tranexamic acid) and arginine hydrochloride.

In some embodiments, the concentration of the anti-fibrinolytic agent such as tranexamic acid in the BAC ranges from about 80 to about 110 mg/ml.

In some embodiments. BAC2 is prepared according to the disclosure of EP 534 178, the content of which is incorporated herein by reference. For example, BAC2 may be prepared from concentrated cryoprecipitate, which thereafter undergoes viral inaction e.g., by solvent detergent treatment and pasteurization.

In some embodiments, the blood derived fibrinogen concentrate is BAC2, namely, a concentrated viral inactivated cryoprecipitate comprising mainly fibrinogen and is plasminogen-depleted (the removal of plasminogen can be carried out as described in EP 1 390 485). In view of removal of plasmin/plasminogen from the cryoprecipitate, there is no need to add anti-fibrinolytic agents, such as, and without being limited thereto, tranexamic acid, aprotinin or the like. Accordingly, in some embodiments, the BAC2 does not comprise tranexamic acid, aprotinin or the like.

In some embodiments, the blood derived fibrinogen concentrate is a byproduct of the manufacture process of factor VIII and may be selected from acid-precipitate, chill-precipitate, aluminum hydroxide precipitate (see, for example, U.S. Pat. No. 4,455,300, the content of which is incorporated herein by reference), glycine precipitate (see, for example, U.S. Pat. No. 4,297,344, the content of which is incorporated herein by reference), ethanol precipitate, and heparin precipitated paste.

In some embodiments, the blood derived fibrinogen concentrate is a by-product of the manufacture process of factor VIII as described e.g., in U.S. Pat. No. 9,328,338, the content of which is incorporated herein by reference.

In some embodiments, cryoprecipitated fibrinogen denotes, without being limited thereto, fresh frozen plasma precipitate following centrifugation containing Total protein—30 to 60 mg/ml; total viable count (TVC) <1000 CFU/ml; Factor XIII, 2 to 9 IU/ml; Fibronectin—0.5 to 6 mg/ml; and Colttable Fibrinogen—18 to 39 mg/ml.

In yet some other embodiments, the blood derived fibrinogen concentrate comprises or is suspended or precipitated Cohn Fraction I, at times, also referred to as "Paste I".

In some embodiments, Cohn fractionation is a process exploiting differences in isoelectric properties of the various plasma proteins and comprises a series of purification steps that involve modifying the pH, ethanol concentration and temperature to separate proteins through precipitation into five "fractions" (I-V). The Cohn process is known also as the cold ethanol precipitation and is described, e.g. in U.S. Pat. No. 2,390,074, and by Cohn et al. (J. Am. Chem. Soc. 68:459, 1945. J. Am. Chem. Soc. 72:465-474, 1950).

Notably, in the context of the present disclosure, when referring to "suspended or precipitated Cohn Fraction F" it is to be understood as encompassing any product of ethanol fractionation whereby at least fibrinogen is precipitated, and not only the Cohn process referred to hereinabove.

In some embodiments, to obtain suspended or precipitated Cohn Fraction I, blood plasma is subjected to ethanol concentration. Specifically, Cohn I precipitate (Fraction I) may be obtained from thawed pooled plasma by precipitation e.g., at −3° C. to −5° C. and neutral pH at 8-10% ethanol concentration.

Fibrinogen concentrate may also be obtained commercially. Examples of fibrinogen include, but are not limited to, fibrinogen component of EVICEL® (i.e. BAC2), fibrinogen component of Tisseel (containing aprotinin, an antifibrinolytic agent).

The plasma derived fibrinogen concentrate can be defined by the amount of clottable proteins therein.

In the context of the present disclosure when referring to a "clottable protein" it is to be understood as encompassing any of the plasma proteins participating in the clotting cascade. As acceptable in the art, clottable proteins include mostly fibrinogen but also some amounts of additional proteins such as, without being limited thereto, Factor XIII, Fibronectin, and Albumin.

The percent (%) of "clottable proteins" may be calculated, for example, from clottable and total protein determinations. The "total protein" may be determined e.g., by diluting a sample in a solubilizing buffer containing 0.2 mol/l sodium hydroxide and 7 mol/l urea, and comparing the absorbance of the samples at 280 nm with that of a similarly treated house standard calibrated against the World Health Organization International Standard (Fibrinogen Human Concentrate 98/614).

The "clottable protein" may be determined by methods known in the art, for example, by clotting a diluted sample with thrombin (e.g., 4 IU/ml), washing the clot with a buffer and thereafter drying the clot on a filter paper. The dry clots may be then dissolved in the solubilizing buffer and the % clottable protein may be determined by comparing the absorbance at 280 nm with that of a similarly treated house standard calibrated against the above-mentioned World Health Organization International Standard.

In some embodiments, the plasma derived fibrinogen concentrate comprises at most 79.8% clottable proteins out of the total amount of protein in the plasma derived fibrinogen concentrate (79.8 mg/ml out of 100 mg/ml total proteins).

In some embodiments, the plasma derived fibrinogen concentrate comprises between 65% to 78%, in some embodiments, between 68% to 78%, in some embodiments, between 68% to 72%, or yet in some embodiments, about 70% clottable proteins.

In some embodiments, the concentrated fibrinogen comprises total protein in the range of about 80 to about 120 mg/ml and clottable protein in the range of about 50 to about 91) mg/ml. In some additional or alternative embodiments, the plasma derived fibrinogen concentrate is characterized by a fibronectin relative concentration, i.e. the proportion of fibronectin relative to fibrinogen, defined as the fibronectin to fibrinogen molar ratio.

In some embodiments, the fibronectin to fibrinogen molar ratio is equal to or above 0.016, or equal to or above (065.

In some embodiments, the fibronectin to fibrinogen molar ratio is at least about 0.068 in some embodiments, at least about 0.078, or, in some embodiments, the ratio is at least 0.1, at least 0.5, at least 1.0, or at least 1.5.

In some embodiments, the fibronectin to fibrinogen molar ratio is equal or below 2, below 1.5, below 1.0, below 0.5, or below 0.1.

In some embodiments, the fibronectin to fibrinogen molar ratio is between 0.1 to 2.0, respectively.

In yet some other embodiments, the fibronectin to fibrinogen molar ratio is between 0.1 to 0.2.

Turning to Factor XIa, it is to be understood as encompassing the natural, blood derived enzyme, recombinant factor XIa or any analog thereof that is capable of activating the substrate factor IX during hemostasis.

In some embodiments, XIa is present at a concentration of between 0.01 to 110 μg/ml, 0.11 to 110 μg/ml, such an amount of higher than 0.11 and up to 110 μg/ml.

In some embodiments, the fibrinogen is derived from concentrated viral inactivated plasma cryo-precipitate.

The term "viral inactivated", or any grammatical inflection thereof, refers both to the situation wherein viruses are maintained in the relevant composition but are rendered non-viable (for example, by dissolving their lipid coat), and/or to the situation wherein viruses are physically removed from the solution (for example, by size exclusion techniques).

Non-limiting viral inactivation procedure comprises one or more steps selected from: solvent/detergent ("S/D") treatment, pasteurization, selective chromatography and nanofiltration.

Typically, but not exclusively, the term "(S/D) treatment" refers to a process that inactivates enveloped or lipid-coated viruses by destroying their lipid envelope. The treatment may be carried out by the addition of detergents (such as, without being limited thereto. Polyethylene glycol 4-tert-octylphenyl ether [TRITON X-45], Octyl phenol ethoxylate [TRITON X-100] and/or Polysorbate [TWEEN 80]), or solvents [such as tri(n-butyl)phosphate (TnBP), di- or trialkylphosphates]. The solvent-detergent combination used to deactivate lipid coated viruses may be any solvent-detergent combination known in the art such as TnBP and Octyl phenol ethoxylate [TRITON X-100]; Polysorbate 80 [TWEEN 80] and Sodium cholate and other combinations. The concentration of the solvent(s) and detergent(s) used can be those commonly used in the art, for example, >0.1% TnBP and >0.1% Octyl phenol ethoxylate [TRITON X-100].

Sometimes a combination of about 1% Octyl phenol ethoxylate [TRITON X-100] and 0.3% to 1% TnBP may be used. Typically, but not exclusively, the conditions under which the solvent-detergent inactivates the viruses consist of 10-100 mg/ml of solvent-detergent at a pH level ranging from 5-8, and a temperature ranging from 2-37° C. for 30 min to 24 hours. However, other solvent-detergent combinations and suitable conditions will be apparent to a person versed in the art.

In some embodiments, the bulk of the solvent-detergent used in the S/D treatment is removed, for example, by using chromatography columns such as hydrophobic interaction chromatography column (HIC) e.g., C-18 silica packing material and SDR (Solvent-Detergent removal) HyperD;

protein adsorption matrices such as ion-exchange matrices; affinity matrices: oil extraction and/or size-exclusion matrices.

The SDR HyperD advantageously involves a mixed-mode adsorption of hydrophobic interaction and is associated with a molecular exclusion effect [Guerrier L et al. "Specific sorbent to remove solvent-detergent mixtures from virus-inactivated biological fluids". J Chromatogr B Biomed Appl. 1995 Feb. 3; 664(1):119-125].

Typically, but not exclusively, "pasteurization" refers to a process by which heat destroys both lipid-enveloped and non-enveloped viruses. "Pasteurization" is interchangeable with the term "heat inactivation" or "heat treatment".

In some embodiments, the heat inactivation is carried out at about 60° C., for about 10 hours. Stabilizers such as sucrose and glycine may be added into a solution during the pasteurization step.

Typically, but not exclusively, "nanofiltration" refers to a process by which lipid-enveloped and non-enveloped viruses are excluded from a solution e.g. by using nanometer-scale filters such as Planova™ 15N, 20N, 35N and 75N; Viresolve/70™, Viresolve/180™. In some embodiments, filters have a pore size of less than 70 nm, e.g., between 15 and 50 nm. However, any membrane having a pore size sufficient to reduce or eliminate viruses from the sample can be employed in nanofiltration.

Viruses removed by nanofiltration may be enveloped (e.g. HIV, hepatitis B virus (HBV), hepatitis C virus (HCV), West Nile Virus, cytomegalovirus (CMV), Epstein-Barr virus (EBV), herpes simplex virus (HSV), and non-enveloped (e.g., hepatitis A virus, parvovirus B19, Polio virus). The solution may be concentrated by ultrafiltration process. In some embodiments, the ultrafiltration can be followed by or preceded by diafiltration to exchange the buffer. The concentration and dialysis by ultrafiltration and diafiltration, respectively, may be carried out in one step or as two separate steps. The diafiltration may be carried out against any solvent or buffer which is suitable for human administration.

In the fibrinogen solution component, the fibrinogen may be dissolved in an appropriate solvent. In some embodiments, the solvent is an aqueous solution. In some embodiments, the solvent comprises water.

The term "appropriate solvent" is intended to mean a solvent or a mixture of several solvents in which the fibrinogen is soluble. By "soluble", it is meant to having solubility of above e.g., 0.1, 0.2, 0.3, 0.4, 0.5, 0.6, 0.7, 0.8, 0.9, or 1 mg/ml.

When referring to an "aqueous solution" it is to be understood to encompass a blend of ingredients, in liquid or frozen, that contains water molecules.

In some embodiments, the aqueous solution comprises at least 50% by weight water. In some embodiments, the aqueous solution comprises at least 95% by weight water or even at least 98% by weight water.

In some embodiments, the aqueous solution is in liquid form. When in liquid form, it is in accordance with some embodiments that the liquid carrier is a buffer having an essentially neutral pH, e.g., pH 7.0±0.5.

In some embodiments the fibrinogen solution component is cell-free. In some embodiments the thrombin component is cell-free By "cell-free" it means with no or substantially no cells (e.g., erythrocytes, leucocytes, thrombocytes, platelets) in a volume of the relevant component.

In some embodiments, the fibrinogen solution component further comprises factor XIII. In some embodiments, the fibrinogen solution comprises factor XIII at a concentration of at least 0.5, at least 0.6, at least 0.7, at least 0.8, at least 0.9, at least 1, at least 1.1, at least 1.2, at least 1.3, at least 1.4, or at least 1.5 IU/ml.

In some embodiments, at least one component of the disclosed two components is devoid of a molecule (such as a protein or a peptide) or a moiety thereof that is capable of specifically binding to fibrinogen except for thrombin.

In some embodiments, the fibrinogen solution component further comprises additional clottable proteins. In some embodiments the additional clottable proteins comprise factor XIII.

In some embodiments, the fibrinogen solution component further comprises plasma proteins, except for albumin, at a concentration of less than 20% of total protein e.g., 1 to less than 20%, by weight. In some embodiments, the fibrinogen solution component further comprises plasma proteins, except for albumin, at a concentration of less 10% of total protein by weight. In some embodiments, the fibrinogen solution component further comprises plasma proteins, except for albumin, at a concentration of less than 5% of total protein by weight. In some embodiments, the fibrinogen solution component is substantially devoid of plasma proteins other than fibrinogen, factor XIII, and albumin.

By "substantially devoid of plasma proteins other than fibrinogen, factor XIII, and albumin" it is meant that plasma proteins other than fibrinogen, factor XIII, and albumin may be present at a concentration of up to 1%, up to 0.5%, up to 0.1%, up to 0.05%, up to 0.01%, or, in some embodiments, the proteins other than fibrinogen, factor XIII, and albumin are completely absent.

In some embodiment, the fibrinogen solution component comprises other plasma proteins at a concentration of less than 20% of total proteins by weight, the other plasma proteins being selected from fibronectin, factor VIII, von Willebrand factor, factor XIII, vitronectin, and any combination thereof. In some embodiments, the fibrinogen solution component does not comprise any of fibronectin, factor VIII, von Willebrand factor, factor XIII, and vitronectin. In some embodiments, the fibrinogen solution component is substantially devoid of fibronectin, factor VIII, von Willebrand factor, and vitronectin.

In some embodiments, the fibrinogen solution component contains albumin and is substantially devoid of plasma proteins other than fibrinogen and albumin.

By "substantially devoid of plasma proteins other than fibrinogen and albumin" it is meant that plasma proteins other than fibrinogen and albumin may be present at a concentration of up to 1%, up to 0.5%, up to 0.1%, up to 0.05%, up to 0.01%, by weight, or, in some embodiments, the proteins other than fibrinogen are completely absent.

As used herein and in the art, "thrombin" or "thrombin polypeptide" is a mammalian serine protease which is part of the blood coagulation cascade and converts fibrinogen into insoluble strands of fibrin, as well as catalyzes other coagulation-related reactions. In the context of the present disclosure, the term "thrombin" is also meant to encompass thrombin functional analog. The term "thrombin functional analog" refers to an entity that is capable of at least cleaving fibrinogen to form fibrin.

In some embodiments, the thrombin component is in a liquid form. The term "liquid form" in the context of the present invention refers to the generally understood state of a fluid in which the fluid has a definite volume without a definite shape except that temporarily given by a container or the like. Unless stated otherwise, "liquid form" does not mean to include gel or gelled. In some embodiments, the liquid thrombin is an aqueous liquid thrombin formulation. In some embodiments, the thrombin is present in an aqueous solution.

In some embodiments, the thrombin is in a powder form. In some embodiments, the powder form of the thrombin is spray-dried thrombin powder.

In some embodiments, the powder form of the thrombin is a dry thrombin powder. By "dry thrombin powder" means that the powder may have moisture content (e.g., as measured by "loss on drying" method) of less than about 5%, less than 2%, or less than 1%, by weight.

In some embodiments, the thrombin component comprises thrombin at a concentration of less than 300 IU/ml. In some embodiments, the thrombin is at a concentration of less than 270 IU/ml, 200 IU/ml, 150 UI/ml, 100 IU/ml, or 50 IU/ml. In some embodiments, the thrombin is present at a concentration of 30 to 270 IU/ml, or 50 to 260 IU/ml. In some embodiments, the thrombin is present at a concentration of 30, 40, 50, 60, 70, 80, 90, 100, 110, 120, 130, 140, 150, 160, 170, 180, 190, 200, 210, 220, 230, 240, 250, or 260 IU/ml, including any value and range therebetween.

As used herein, the term "IU" denotes "International Units" and may be determined by the clotting assay against an internal reference standard for potency concentration measurement that has been calibrated against, for example, the World Health Organization (WHO) Second International Standard for Thrombin, 01/580. A unit (U) is equivalent to an International Unit (IU). In some embodiments, the thrombin component comprises calcium e.g. at a concentration of about 35 Mm to 45 mM.

The fibrinogen-containing component may comprise plasma proteins other than fibrinogen and albumin. In some embodiments, the plasma proteins other than fibrinogen may be present]. Non-limiting examples of plasma proteins other than fibrinogen and albumin include naturally occurring plasma proteins, such as fibronectin, factor VIII, von Willebrand factor, factor XIII, and vitronectin.

As noted herein, the kit comprises a second compartment comprising thrombin. Thrombin is a mammalian serine protease which is part of the blood coagulation cascade and converts fibrinogen into insoluble strands of fibrin, as well as catalyzes other coagulation-related reactions. In the context of the present disclosure, the term "thrombin" is also meant to encompass thrombin functional analog. The term "thrombin functional analog" refers to an entity that is capable of at least cleaving fibrinogen to form fibrin.

The "thrombin-containing component" is to be understood as a formulation comprising a priori thrombin an optionally additional proteins such as albumin. The thrombin-containing component may be in a liquid form or in a frozen form. The thrombin-containing component may be manipulated before use, for example by thawing if present in a frozen form.

In some embodiments, the thrombin-containing component comprises between about 100 IU/ml to about 300 IU/ml thrombin. In some embodiments, the thrombin-containing component comprises between about 100 IU/ml to about 200 IU/ml thrombin. In some embodiments, the thrombin-containing component comprises between about 150 IU/ml to about 200 IU/ml thrombin.

In some embodiments, the thrombin-containing component comprises a diluted thrombin component of EVICEL®. In some embodiments, the thrombin-containing component comprises the thrombin component of EVICEL® diluted by at least a factor of two. In some embodiments, the thrombin-containing component comprises the thrombin component of EVICEL® diluted by a factor of between two to ten. In some embodiments, the thrombin-containing component comprises the thrombin component of EVICEL® diluted by a factor of two. In some embodiments, the thrombin-containing component comprises the thrombin component of EVICEL® diluted by a factor of four. In some embodiments, the thrombin-containing component comprises the thrombin component of EVICEL® diluted by a factor of eight.

A variety of buffers may be used for the dilution of thrombin-containing component. In some embodiments, the buffer comprises at least one of sodium acetate trihydrate, D-mannitol, calcium chloride dihydrate and sodium chloride. In some embodiments, the buffer comprises about 20 mM sodium acetate trihydrate, about 0.1 mM D-mannitol, about 40 mM calcium chloride dihydrate and about 90 mM sodium chloride. In some embodiments, the buffer has a pH value of 6.8-7.2. An exemplary buffer is as shown in Table 3 below.

The fibrinogen-containing component and a thrombin-containing component may be mixed prior to the application on the target tissue or administered simultaneously on the target tissue.

As noted above, thrombin converts fibrinogen into fibrin that undergoes spontaneous polymerization. However, for stabilization of a clot, cross linked fibrin is required that takes place by Factor XIII in the presence of divalent ions such as calcium ions. In other words, for stabilizing a clot, the presence of calcium ions is required. The fibrinogen-containing component and/or the thrombin-containing component comprises free calcium ions. In some embodiments, the free calcium ions are ionized and non-chelated calcium.

In some embodiments, at least one or, in one embodiment, the two components of the fibrinogen solution component and the thrombin component comprise a protein additive e.g., albumin. In some embodiments, the fibrinogen solution component comprises a protein additive e.g., albumin. In some embodiments, the thrombin component comprises a protein additive e.g., albumin. In some embodiments, the protein additive e.g., albumin is the main protein (i.e. more than 50% by weight) present in the fibrinogen component.

As used herein, the term "protein additive" refers to a protein which may interact reversibly with thrombin in an aqueous solution, i.e. without affecting the fibrinogen and/or thrombin activity or structure.

Non-limiting exemplary protein additives are selected from immunoglobulins, caseins and albumins.

In exemplary embodiments, the protein additive is or comprises albumin. In some embodiments, the albumin is selected from, without being limited thereto, human albumin, non-human albumin, recombinant albumin, and any combination thereof.

In some embodiments, the albumin is human serum albumin (HSA). In some embodiments, the albumin is present in the fibrinogen solution component at a concentration of at least 65%, or in some embodiments, at least 75% of the total proteins, by weight. In some embodiments, the albumin is present in the fibrinogen solution component at a concentration of at 65% to 80% of the total proteins by weight.

In some embodiments, the albumin is present in the fibrinogen solution component at a concentration of between 50 to 120, or 60 to 110 mg/ml. In some embodiments, the albumin is present in the fibrinogen solution component at a concentration of 50, 60, 70, 80, 90, 100, 110, or 120 mg/ml, including any value and range therebetween.

Additionally, or alternatively, in some embodiments, the albumin is present in the thrombin solution component at a concentration of between 4 to 8 mg/ml, or 5.0-6.5 mg/ml.

e.g., 4, 4.5, 5, 5.5, 6, 6.5, 7, 7.5, or 8 mg/ml, including any value and range therebetween.

According to another aspect, the present application provides anti-adhesive curable composition comprising fibrin at a concentration of about 2-15 mg/ml, thrombin at a concentration of about 40-180 IU/ml or 50 to 150 IU/ml, calcium, and about 20-80 mg/ml total proteins.

It is appreciated that formation of a curable solution following mixing the two components is dependent on the presence of both fibrinogen and thrombin. Accordingly, in the absence of thrombin, the composition is not curable.

The term "curable" refers to the capability of the composition (i.e. the combined product) to increase its viscosity. e.g., to form a gel such as a hydrogel. Such increased viscosity may be obtained by interactions including polymerization and/or cross-linking of protein components (e.g., fibrin) in the composition. The temperature at which the curing reaction may be conducted may be at around the room temperature (e.g., 15 to 30° C.). In some embodiments, the may be in the range of seconds and up to 600 seconds. The term "curing time" means the time until an endpoint of the curing is reached.

The term "gel" refers to substantial liquid dispersed in a solid. Typically, a gel has properties of the solid state, and under certain conditions (e.g., temperature, pH) exhibits properties of the liquid state. In some embodiments, the gel is a hydrogel. The term "hydrogel" is intended to refer to hydrophilic polymeric networks having water content.

The term "liquid" relates to a substance that can flow, has not fixed shape, and is not a solid or gas.

The term "solution" relates to dispersed or dissolved substance(s) and the medium in which it is dispersed or dissolved or to a single homogeneous liquid phase that is a mixture in which the components are uniformly distributed throughout the mixture.

The term "component" relates to any ingredient which may be present in a product, such as a drug product.

"Derived" relates to received from a source. For example, "derived from" relates to taken from, obtained from, received from.

Total protein may be determined by any method known in the art. For example, by measuring absorbance at 280 nm (UV range).

In some embodiments, the curing is carried out spontaneously at ambient conditions.

In some embodiments, the curing is implemented by one or more methods including, without being limited thereto: by use of an activator (such as a catalyst), by a physical activating agent, such as heat, or ultra-violet UV radiation.

In some embodiments, the anti-adhesive curable composition comprises fibrinogen or fibrin at a concentration in the range of about 2-15, or 5-10 mg/ml, thrombin at a concentration in the range of about 40-180 IU/ml or 50 to 150 IU/ml, and calcium.

According to another aspect, the present application provides an anti-adhesive curable composition comprising fibrinogen at a concentration in the range of about 2-15 mg/ml, thrombin at a concentration in the range of about 40-180 IU/ml or 50 to 150 IU/ml and calcium.

According to another aspect, the present application provides an anti-adhesive curable composition comprising fibrinogen at a concentration in the range of about 2-15 mg/ml, thrombin at a concentration in the range of about 40-180 IU/ml or 50 to 150 IU/ml, calcium, and albumin.

According to another aspect, the present application provides an anti-adhesive curable composition comprising fibrin at a concentration in the range of about 2-15 mg/ml, thrombin at a concentration in the range of about 40-180 IU/ml or 50 to 150 IU/ml, and albumin.

According to another aspect, the present application provides an anti-adhesive curable composition comprising fibrin at a concentration in the range of about 2-15 mg/ml, thrombin at a concentration in the range of about 40-180 IU/ml or 50 to 150 IU/ml, calcium, and albumin.

According to another aspect, the present application provides hydrogel composition comprising fibrin, thrombin, calcium and albumin, wherein the fibrin is present at a concentration in the range of 3 to 15% of a total protein weight, the thrombin is present at a concentration in the range of about 50 to 150 IU/ml, and the albumin is present at a concentration of at least 60% of total protein by weight.

According to another aspect, the present application provides a hydrogel composition comprising fibrin, thrombin, and calcium, wherein the fibrin is present at a concentration in the range of about 3 to 15% of a total protein weight, and the thrombin is present at a concentration of about 50 to 150 IU/ml.

According to another aspect, the present application provides a hydrogel composition comprising fibrin, calcium and thrombin, wherein the fibrin is present at a concentration in the range of about 3 to 15% of a total protein by weight, the total protein concentration ranges from about 80 to about 120 mg/ml, and the thrombin is present at a concentration in the range of about 50-150 IU/ml.

According to another aspect, the present application provides a hydrogel composition comprising: calcium, in the range of about 5-10 mg/ml fibrin, in the range of about 50-150 IU/ml thrombin, and optionally further comprising in the range of about 15-60 mg/ml albumin.

According to another aspect, the present application provides a hydrogel composition comprising: calcium, in the range of about 40-65 mg/ml total protein, in the range of about 5-10 mg/ml fibrin, in the range of about 50-150 IU/ml thrombin, and optionally further comprising in the range of about 15-60 mg/ml albumin.

In exemplary embodiments of any aspect of the hydrogel composition or the curable composition, the composition comprises fibrin at a concentration in the range of about 4-10 mg/ml, thrombin at a concentration in the range of about 50-150 IU/ml, and a concentration in the range of about 40-60 mg/ml total proteins.

In some such embodiments of any aspect of the hydrogel composition, the calcium is present at a concentration in a range of about 15 mM to 25 mM, or 18 µM to 22 mM.

In some embodiments of any aspect of the hydrogel composition and the curable composition, the composition comprises fibrin at a concentration of about 4, 5, 6, 7, 8, 9, or 10 mg/ml, including any value and range therebetween.

In some embodiments of any aspect of the curable composition, the composition comprises fibrinogen at a concentration of about 4, 5, 6, 7, 8, 9, or 10 mg/ml, including any value and range therebetween.

In further such embodiments of any aspect of the hydrogel composition and the curable composition, the composition comprises thrombin at a concentration of 50, 60, 70, 80, 90, 100, 110, 120, 130, 140, or 150 IU/ml, including any value and range therebetween.

In further such embodiments of any aspect of the hydrogel composition and the curable composition, the composition comprises 40, 45, 50, 55, 60 or 65 mg/ml total proteins, including any value and range therebetween.

In some embodiments of any aspect provided herein, the anti-adhesive curable composition essentially comprises fibrinogen and thrombin. In some embodiments, the anti-adhesive curable composition essentially comprises fibrinogen, albumin and thrombin. Herein, by "essentially comprises fibrinogen and thrombin", it is meant that the total concentration (by weight) of fibrinogen and thrombin, is at least 95%, at least 96%, at least 97%, at least 98%, or at least 99%, of the composition. Accordingly, by "essentially comprises fibrinogen, albumin and thrombin" it is meant that the total concentration (by weight) of, fibrinogen albumin, and thrombin is at least 95%, at least 96%, at least 97%, at least 98%, or at least 99%, of the composition.

In some embodiments of any aspect provided herein, the anti-adhesive curable composition essentially comprises fibrin and thrombin. In some embodiments, the anti-adhesive curable composition essentially comprises fibrin, albumin and thrombin. Herein, by "essentially comprises fibrin and thrombin", it is meant that the total concentration (by weight) of fibrin and thrombin, is at least 95%, at least 96%, at least 97%, at least 98%, or at least 99%, of the composition. Accordingly, by "essentially comprises fibrin, albumin and thrombin" it is meant that the total concentration (by weight) of fibrin, albumin, and thrombin is at least 95%, at least 96%, at least 97%, at least 98%, or at least 99%, of the composition.

In some embodiments of any aspect of the hydrogel composition and the curable composition, the composition further comprises plasma proteins at a concentration of more than 20% of total protein by weight.

In some embodiments of any aspect of the hydrogel composition and the curable composition, the composition further comprises plasma proteins, except for albumin, at a concentration of less than 20% of total protein by weight. In some such embodiments, the composition further comprises plasma proteins, except for albumin, at a concentration that does not exceed 10% of total protein by weight. In some such embodiments, the composition further comprises plasma proteins, except for albumin, at a concentration that does not exceed 5% of total protein by weight. In some such embodiments, the composition is substantially devoid of plasma proteins other than fibrin and albumin. In some such embodiments, the composition is substantially devoid of plasma proteins other than fibrinogen, Factor XIII, and albumin.

In some embodiments, the curable composition is post-surgical adhesion prevention composition (e.g., in the form of lubricant).

Accordingly, in some embodiments, the two-component anti-adhesive kit of the invention is used for preventing tissue adhesion following invasive procedures such as surgical procedures, during post-operative procedures, or during laparoscopic procedures including procedures such as, and without being limited thereto, resolving intestinal obstruction, and abdominal or genecology surgery. The invasive procedure may be in accordance with some other embodiments, a diagnostic procedure.

Further non-limiting exemplary surgical procedures include a procedure selected from, cardiovascular surgery, thoracic surgery, head and neck surgery, pelvic surgery, and a skin and subcutaneous tissue procedure.

The two-component curable anti-adhesive composition may be provided by combining (e.g., upon mixing) the two components, thereby obtaining a composition, and simultaneously, or thereafter, applying the obtained composition directly to the site where adhesion prevention is needed. In some embodiments, the application of the composition is assisted by spraying or dripping the composition onto the area to be treated.

In some embodiments, combining (e.g., by mixing) the two components as disclosed herein according to any of the embodiments mentioned hereinthroughout gives rise to a composition (e.g., in the form of a mixture) having anti-adhesive properties. The composition may be in the form of a curable or cured gel which may be applied to the site where adhesion prevention is needed. The cured gel functions as a barrier to prevent adhesion of the tissues on either side of the gel. One of the most common uses for this gel is to prevent adhesions following or during invasive procedures, such as surgical procedures.

In some embodiments of any aspect provided herein, is the hydrogel or the anti-adhesive curable composition (e.g., the hydrogel as disclosed herein).

In some embodiments, the pressure is a compression pressure. The term "compression pressure" refers to a pressure utilized to compress a sample into a more compressed form than the initial state (prior to applying the compression pressure).

Without being bound by any particular theory or mechanism, it may be assumed that a capability of the hydrogel composition to release liquid (e.g., water) therefrom allows to generate more compressed fiber network of the anti-adhesive composition. That is, for example in a condition in which a high pressure is applied on the disclosed composition, e.g., by a bodily organ, such as peristaltic organ, the composition may form a small thickness film, thereby reducing the likelihood of stimulating an immune system response and/or interfering with the normal action of the organ, and at the same time, increasing the biodegradation rate of the composition.

Without being bound by any particular theory or mechanism, it may be further assumed that the presence of albumin in the formulation might affect (decrease) the crosslinking degree of fibrin net of the formed clot, which in turn leads to the increased loss of the water content by the clot.

Accordingly, there is provided a method of increasing the release rate of a liquid (e.g., water) from a hydrogel composition under high pressures (e.g., 25 atm or more, e.g., at about 30 atm), the method comprising incorporating albumin in the hydrogel composition. In some embodiments, the albumin is present at a concentration ranging from 60 to 110 mg/ml, e.g., 60, 70, 80, 90, 100, or 110 mg/ml. In some embodiments of this aspect, the composition comprises fibrin and thrombin. In some embodiments of this aspect, the composition comprises fibrin thrombin, and calcium. In some embodiments of this aspect, the composition comprises calcium, about 5-10 mg/ml fibrin, and about 50-150 IU/ml thrombin. In some embodiments of this aspect, the composition comprises about 5-10 mg/ml fibrin, and about 50-150 IU/ml thrombin. In some embodiments, the incorporation of the albumin is carried out during the preparation of the hydrogel composition.

In some embodiments, the disclosed hydrogel (or the curable composition) is characterized in that it does not exert a hemostatic activity, i.e., it does not reduce bleeding.

By "does not exert a hemostatic activity" it is meant that the disclosed composition (upon contacting a bleeding site) is capable of reducing less than 30%, less than 20%, less than 10%, less than 5%, or even 0%, compared to the initial bleeding rate, i.e. prior to applying the composition onto the bleeding site.

It is appreciated that all embodiments mentioned above with reference to the two-component anti-adhesive of the invention also apply to this aspect.

It is appreciated that all embodiments mentioned above with reference to the anti-adhesive curable or hydrogel composition or its components and that do not extend outside the scope of the above aspects are all meant to be included in the above aspects.

As described herein, in some embodiments, the curable composition is formed from the two components by combining the components. The components may be combined by any reasonable means. In exemplary embodiments, the EVICEL® device may be used, wherein the fibrinogen solution component is loaded onto one syringe, the thrombin component is loaded into the other, and the two components are pushed together out of the syringes to mix in a common conduit out of which the mixture is thereafter directly applied to the desired target site. In such exemplary embodiments, the components are prepared such that they may be mixed together at a ratio of about 1:1, for convenience. However, other or further settings, applicators, and ratios may be conceived of so as to obtain the desired curable composition as disclosed herein in any embodiment thereof.

Accordingly, in an additional aspect, the present invention provides a method of preparing an anti-adhesion curable composition ("the preparation method") comprising the following steps:
  i. providing a fibrinogen solution having at a fibrinogen concentration ranging from 5% to 30%, or from 8% to 25% of total protein by weight, wherein the total protein concentration ranges from about 50 to 150 mg/ml, or 80 to 120 mg/ml;
  ii. providing thrombin; and
  iii. combining the fibrinogen solution with the thrombin, thereby obtaining a curable composition.

In some embodiments, the method further comprises providing calcium and combining thereof with the fibrinogen solution and/or the thrombin. In some embodiments, the fibrinogen solution comprises calcium. In some embodiments, the thrombin comprises calcium. Embodiments of the calcium and a concentration thereof are provided hereinabove in the context of the disclosed kit, and are further incorporated herein.

In some embodiments, the total protein content (in the fibrinogen solution) comprises at least 65%, or at least 75% albumin, by weight. In some embodiments, the total protein content comprises 65% to 90% albumin, by weight.

In a further aspect, there is provided a method of preparing an anti-adhesive curable composition comprising the step of: combining: (i) a fibrinogen solution component comprising fibrinogen at a concentration of about 5 to 40 mg/ml, e.g., 10 to 20 mg/ml; (ii) a thrombin component comprising thrombin;

In some embodiments, the method further comprises providing calcium and combining thereof with the fibrinogen solution and the thrombin. In some embodiments, the fibrinogen solution comprises calcium. Embodiments of the calcium and a concentration thereof are provided hereinabove in the context of the disclosed kit, and are further incorporated herein.

In some embodiments of any aspect of the preparation method provided herein, the thrombin is present in a liquid solution at a concentration of 100 to 300 IU/ml.

In some embodiments of any aspect of the preparation method, the fibrinogen solution and the thrombin are combined in a ratio (v/v) of 1:1.2 to 1.2:1 thereof.

In some embodiments of any aspect of the preparation method the thrombin is in the form of a powder.

In exemplary embodiments, the final concentrations in the anti-adhesion curable composition obtained after combining are: 40-65 mg/ml total protein, 5-10 mg/ml fibrinogen, 50-150 IU/ml thrombin, and about 30-60 mg/ml albumin In some embodiments, the thrombin component is in a powder form.

In some embodiments, the thrombin is a liquid form and is present in the thrombin component at a concentration of 50-300 IU/ml.

In some embodiments, the combining at step (iii) is carried out with approximately equal volumes of the fibrinogen solution component and the thrombin component.

By "approximately equal volumes" it is meant to refer to a volume ratio of 1.2:1 to 1:1.2, e.g., about 1:1.

In a further aspect, the present invention provides a cured gel formed by the method of the invention in an embodiment thereof.

In yet a further aspect, the present invention provides a method for preventing tissue adhesion ("anti-adhesion prevention method") comprising the following steps:
  a. providing a fibrinogen solution component comprising fibrinogen at a concentration of below 8 to 30, or 8% to 25% of total protein by weight, and a total protein concentration of about 80 to 120 mg/ml;
  b. providing a thrombin component comprising liquid thrombin at a concentration of 50-300 IU/ml; and
  c. simultaneously spraying or dripping the fibrinogen solution component and the thrombin component onto the desired location.

In some embodiments, the anti-adhesion prevention method further comprises providing calcium and combining thereof with the fibrinogen solution and the thrombin. In some embodiments, the fibrinogen solution comprises calcium. In some embodiments, the thrombin component comprises calcium. Embodiments of the calcium and a concentration thereof are provided hereinabove in the context of the disclosed kit, and are further incorporated herein.

In some embodiments, the total protein content comprises at least 65%, or at least 75% albumin, by weight. In some embodiments, the total protein content comprises 65% to 90% albumin, by weight.

The term "simultaneously" used hereinthroughout does not necessarily mean the same time, and may also refer, in the relevant context, to a case of first spraying or dripping the fibrinogen solution component and shortly thereafter spraying or dripping the thrombin component, or to a case of first spraying or dripping the thrombin component and, immediately thereafter, spraying or dripping the fibrinogen solution component. Herein, by "immediately" it is meant to refer to within 0 to 20 sec, 0 to 10 sec, or 0 to 2, e.g., 0, 1, 2, 3, 4, 5, 6, 7, 8, 9, 10, 11, 12, 13, 14, 15, 16, 17, 18, 19, or 20 sec, including any value and range therebetween.

In yet a further aspect, the present invention provides a method for preventing tissue adhesion ("anti-adhesion prevention method") comprising the following steps:
  a. providing a fibrinogen solution component comprising fibrinogen solution component comprising fibrinogen at a concentration of about 5 to 40 mg/ml, or 10 to 20 mg/ml;
  b. providing a thrombin component comprising liquid thrombin at a concentration of 50-300 IU/ml; and
  c. simultaneously spraying or dripping the fibrinogen solution component and the thrombin component onto the desired location.

In some embodiments, the anti-adhesion prevention method in any aspect thereof further comprises providing calcium and combining thereof with the fibrinogen solution and the thrombin. In some embodiments, the fibrinogen solution comprises calcium. In some embodiments, the thrombin solution comprises calcium. Embodiments of the calcium and a concentration thereof are provided hereinabove in the context of the disclosed kit, and are further incorporated herein.

In some embodiments of any aspect of the anti-adhesion prevention method provided herein, the fibrinogen solution and the thrombin are combined in a ratio (v/v) of 1:1.2 to 1.2:1 thereof.

In some embodiments of any aspect of the anti-adhesion prevention provided herein the thrombin component comprises less than 10 ppm of chelating agent.

According to another aspect, there is provided a two-component composition comprising: component A comprising a fibrinogen solution comprising a fibrinogen at a concentration of 8% to 25% of total protein by weight, and optionally free calcium ions at a concentration ranging from 0.1 µM to 1 mM; wherein a total protein concentration ranges from about 80 to 120 mg/ml; and component B comprising a thrombin component that. In some embodiments, the combination of components A and B, gives rise to an anti-adhesives curable mixture.

Embodiments of the calcium and a concentration thereof are provided hereinabove in the context of the disclosed kit, and are further incorporated herein.

According to another aspect, there is provided a two-component curable composition comprising: component A comprising a fibrinogen solution comprising fibrinogen at a concentration of about 5 to 25 mg/ml; and free calcium ions at a concentration ranging from 0.1 µM to 1 mM; and component B comprising a thrombin component. In some embodiments, a combination of components A and B gives rise to an anti-adhesives curable mixture.

The two-component composition may be used for anti-adhesion prevention. In some embodiments, the two-component composition is a curable composition.

In some embodiments, the fibrinogen solution comprises calcium. Embodiments of the calcium and a concentration thereof are provided hereinabove in the context of the disclosed kit, and are further incorporated herein.

In some embodiments of any aspect of the two-component composition, the thrombin component comprises free calcium ions.

In some embodiments of any aspect of the two-component composition, the thrombin component is devoid of chelating agent.

In some embodiments of any aspect of the two-component curable composition, the fibrinogen in the fibrinogen component is present at a concentration of 10 to 20 mg/ml.

In some embodiments of any aspect of the two-component curable composition, the thrombin component is in the form of a liquid solution.

In some embodiments of any aspect of the two-component curable composition, the thrombin is present in the thrombin solution at a concentration ranging from 100 to 300 IU/ml.

In some embodiments of any aspect of the two-component curable composition, the component A and the component B are present at a ratio ranging from 1.2:1 to 1:1.2, by volume.

In exemplary embodiments of any kit, two-component curable composition, or method provided herein, the fibrinogen component comprises fibrinogen, Human albumin, Sodium Chloride, Citrate, Arginine Hydrochloride, and Glycine.

In exemplary embodiments of any kit, two-component curable composition, or method provided herein, the fibrinogen component comprises fibrinogen at a concentration of 10-20 mg/ml, Human albumin at a concentration of 60-110 mg/ml, Sodium Chloride at a concentration of 120 mM, Citrate at a concentration of 2.2-3.1 mg/ml, Arginine Hydrochloride at a concentration of 18.5-22.5 mg/ml, and Glycine at a concentration of 7.0-9.0 mg/ml. In exemplary embodiments, the fibrinogen component comprises total protein at a concentration of 80-120 mg/ml.

In exemplary embodiments of any kit, two-component curable composition, or method provided herein, the thrombin component comprises thrombin, human albumin, acetate, mannitol, and calcium.

In exemplary embodiments of any kit, two-component curable composition, or method provided herein, the thrombin component comprises thrombin at a concentration of 100 to 300 IU/ml, human albumin at a concentration of 5.0-6.5 mg/ml, acetate at a concentration of 18-20 mM, mannitol at a concentration of 18.5-20.5 mg/ml, and calcium at a concentration of 38-42 mM. In exemplary embodiments, the thrombin component comprises total protein at a concentration of 5 to 6.5 mg/ml.

The terms "inhibiting" and "preventing" are used interchangeably herein throughout.

The term "inhibit" or "inhibition", as used herein, means the restriction, retardation, reduction, decrease or diminishing or preventing of a process, a phenomenon or a phenotype by at least about 1%-100%, about 5%-95%, about 10%-90%, about 15%-85%, about 20%-80%, about 25%-75%, about 30%-70%, about 35%-65%, about 40%-60% or about 45%-55%. Said restriction, retardation, reduction, decrease or diminishing of a process, a phenomenon or a phenotype may also be by at least about 1%, 2%. 3%, 4%, 5%, 6%, 7%, 8%, 9%, 10%, 11%, 12%, 13%, 14%, 15%, 16%, 17%, 18%, 19%, 20%. 21%, 22%, 23%, 24%. 25%, 26%, 27%, 28%. 29%, 30%, 31%, 32%. 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64-%, 65%, 66%, 67%, 68%, 69%, 70%, 71%, 72%, 73%, 74%, 75%, 76%, 77%, 78%, 79%, 80%, 81%, 82%. 83%, 84%, 85%, 86%. 87%, 88%, 89%, 90%. 91%, 92%, 93%, 94%. 95%, 96%, 97%, 98%, 99% or about 100%.

As used hereinthroughout the term "about" refers to ±10%.

The terms "comprises", "comprising", "includes", "including", "having", and their conjugates mean "including but not limited to". The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

In those instances where a convention analogous to "at least one of A, B. and C, etc." is used, in general such a construction is intended in the sense one having skill in the art would understand the convention (e.g., "a composition having at least one of A, B. and C" would include but not be limited to compositions that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

The invention will now be demonstrated by the following non-limiting Examples.

EXAMPLES

Example 1: Evaluation of Adhesions in a Rabbit Uterine Horn Model

This model has been used extensively for the determination of efficacy of putative anti-adhesion agents, and good correlations exist between data obtained in animals and that obtained clinically (Wiseman D M, Gottlick-Iarkowski L, Kamp L. Prevention of Bowel Adhesions Using Two Barriers of Oxidized Regenerated Cellulose (ORC). J Inv Surg 12:141-146 (1999); "Wiseman, 1999").

Briefly, adhesion prevention was evaluated using the uterine horn model in rabbits as previously described (Wiseman D M, Gottlick L E, Diamond M P. Effect of thrombin-induced hemostasis on the efficacy of an absorbable adhesion barrier. J. Reprod. Med. 37:766-770 (1992): "Wiseman 1992"). Six female New Zealand White rabbits were used for each of the following groups: 1) No treatment; 2) Treatment with 32 mg/ml fibrinogen (derived from cryoprecipitate) and 512 IU/ml Thrombin: 3) Treatment with 12 mg/ml fibrinogen (derived from cryoprecipitate) and 260 IU/ml Thrombin; 4) Treatment with Seprafilm®. Briefly, uterine horns were abraded by scraping with a scalpel blade 40 times on each side of each uterine horn and the experimental treatment was applied. After 15-16 days, adhesions were evaluated by estimating the extend of adhesions, the severity of adhesions and the degree of uterine convolution, a measure of anatomical distortion due to adhesions.

More details of exemplary procedures are provided below.

Materials and Methods

EVICEL®-derived Formula #1 was an FDA approved commercially marketed product from which the biological components were taken and diluted by a factor of 2. The dilution was carried out by the addition of appropriate surrogate liquid to each of the biological components.

EVICEL®-derived Formula #2 was an FDA approved commercially marketed product from which the biological components were taken and diluted by a factor of 4. The dilution was carried out by the addition of appropriate surrogate liquid to each of the biological components.

First Component of Test Material: Diluted BAC2

Denomination: BAC2, thawed and diluted by a factor of 2 (Formula #1 or by a factor of 4 (Formula #2) with BAC2 surrogate (see Table 1).

Supplier: Omrix Biopharmaceuticals Ltd.

Protein concentration: Target: 80-120 mg/ml. Actual: 85 mg/ml (Formula #1) and 83 mg/ml (Formula #2)

Clottable Fibrinogen: Target: 27-43 mg/ml (Formula #1) or 13-22 mg/ml (Formula #2). Actual. 32 mg/ml (Formula #1) and 12 mg/ml (Formula #2)

Quantity required: at least 12 vials×2 ml per formula

Storage conditions: ≤−18° C. until use.

Hazards: Handle material with gloves, as with all blood products.

Second Component of Test Material: Diluted Thrombin

Denomination: Thrombin 1000 IU/ml and diluted by a factor of 2 or by a factor of 4 with Thrombin surrogate (see Table 1).

Supplier: Omrix Biopharmaceuticals Ltd.

Protein concentration: Target: 5.5-6.5 mg/ml. Actual: 5.9 mg/ml (Formula #1) and 6.0 mg/ml (Formula #2)

Thrombin concentration: 400-600 IU/ml (Formula #1) or 200-300 IU/ml (Formula #2). Actual: 512 IU/ml (Formula #1) and 260 IU/ml (Formula #2) Quantity required: at least 12 vials×2 ml per formula Storage conditions: ≤−18° C. until use.

Hazards: Handle material with gloves, as with all blood products.

BAC2 surrogate and Thrombin surrogate formulas are provided in Table 1 below.

TABLE 1

BAC2 surrogate and Thrombin surrogate formulas

| Material | Reagent | Concentration |
|---|---|---|
| BAC2 Surrogate | Sodium Chloride | 120 mM |
| | Tri-Sodium Citrate dihydrate | 10 mM |
| | Glycine | 120 mM |
| | Arginine hydrochloride | 9.5 mM |
| | Calcium chloride dihydrate | 1 mM |
| | Human albumin | 11% |
| | pH | 7.0-7.2 |
| Thrombin Surrogate | Sodium Acetate trihydrate | 20 mM |
| | D-Mannitol | 0.1M |
| | Calcium chloride dihydrate | 40 mM |
| | Human Albumin | 0.6% |
| | Sodium Chloride | ~90 mM |
| | pH | 6.8-7.2 |

Following dilution, the samples were filtered through 0.2 μm Polyethersulfone (PES) membrane filter, filled into 2 ml vials, capped with a manual crimper and stored at ≤−18° C. until shipment to Synechion.

Reference Materials: No treatment—Surgery alone. Seprafilm® Adhesion Barrier: Seprafilm Adhesion Barrier (Lot 7BYSEP041, exp 2020-05-31) was obtained from Sanofi-Aventis U.S. LLC, Bridgewater, N.J.

Applicator devices for EVICEL® formulations: The EVICEL® Application Device with the EVICEL® Airless Spray Accessory was used to apply the EVICEL®-derived formulations according to the Assembly guide and the manufacturer instructions.

Acclimation: Animals were examined by experienced animal care personnel shortly after arrival at the test facility. Animals were acclimated for a minimum of 5 days prior to initiation of the study and monitored by experienced animal care personnel daily. Animals supplied for this study were used only if they appeared grossly normal (i.e. showing a clean unruffled coat, bright clear eyes, no unusual exudate from body orifices, alert and active posture).

Housing environment and husbandry: Animals were individually housed in stainless steel cages, each labeled with an individual card indicating the study number and the individual animal number. The room environment was maintained at approximately 68° F. (20° C.) with 30-70% relative humidity and a light/dark cycle of 12 hours/12 hours.

Diet and Water: Purina Prolab Rabbit diet 15% protein (LabDiet, St. Louis, Mo.) and tap water was provided ad libitum to the animals for the duration of the study. Carrots and alfalfa cubes were provided to the rabbits.

Pre-Operative Preparation: Animals were weighed on the day of surgery. Anesthesia was induced and maintained by inhalation of isoflurane (5% and 3.5% concentration, respectively). Depilation of the surgical site was accomplished with an electric animal clipper. The area was vacuumed to remove hair clippings and debris, and then rinsed with isopropyl alcohol 70%. The bladder was expressed (i.e. manipulated externally to force urine out of it). The entire area was painted with an aqueous iodophor solution (iodine scrub) of 1% available iodine. The area was then be swabbed with 70% isopropyl alcohol solution.

Procedures were performed in a sterile manner in a room reserved for aseptic survival surgery. Sterile towels, drapes, and instruments were used. The anesthetized and surgically prepared rabbit was delivered to the operating table and restrained via the limbs in the desired recumbent position. A sterile incise drape was applied to the prepared area.

Animals were randomized in blocks of 4 to one of the study groups by lottery by a disinterested individual. Surgery was conducted on two study days with half the animals from each group being allocated to each study day.

Intra-Operative Procedure: The rabbit uterine horn simple abrasion model was conducted as described by Wiseman et al., 1992. The abdomen was entered via a midline laparotomy incision about 6 cm long. The bladder and uterus were delivered into the wound.

Only those animals with two uterine horns with a diameter of between 9 and 16 French, inclusive, were entered into the study. Using a number 10 scalpel blade, 5 cm lengths of uterine horn, approximately 1 cm from the uterine bifurcation, were scraped. 40 times per side. Hemostasis was controlled by tamponade with gauze. If necessary, small vessels are ligated.

After abrasion procedures were completed per animal, the group assignment was revealed to the surgeon. Test materials were applied to the uterine horn. Organs were repositioned anatomically. During the treatment, the animals were observed carefully to remove any animal with unexpected response to the anesthetic treatment.

Study Arms Application: Reference Control—Controls consisted of animals in which all surgical procedures have been performed, but without the application of test materials.

EVICEL® derived Formula 1 and Formula 2 Treatments: at least 4 vials of 2 ml of each component per animal were thawed at room temperature before induction of anesthesia. Each product was handled according to the EVICEL®) manufacturer's instructions and delivered by spraying using the Omrix application Airless spray device. Enough product was applied so as to cover the traumatised surfaces with a thin film. The volume applied was recorded.

Seprafilm Standard Treatment Control: An approximately 2×3" piece of Seprafilm was draped over each uterine horn before replacing the uterus anatomically.

Post-Operative Procedure: Abdominal incisions were closed using a continuous Vicryl 4-0 suture. Fascia was closed loosely with 4-0 Vicryl and the skin closed with undyed 4-0 Vicryl (cutting needle) using a subcuticular suturing method.

Three doses of buprenorphine (Buprenex) (0.03 mg/kg, 0.4 ml×0.3 mg/ml) were given by subcutaneous injection, one on the morning of surgery, one six to eight hours later and one the following morning. Further doses were given if deemed necessary by the veterinarian.

Clinical Signs of Animals: All animals were observed closely until vertical recumbency was resumed, when they were returned to their cages. Rabbits were placed under a heat lamp or on a heating blanket for this initial post-operative period.

Each rabbit was observed daily after surgery to determine its health status on the basis of general attitude and appearance, food consumption, weight loss, fecal and urinary excretion and presence of abnormal discharges. Animals were observed daily for incisional integrity, excessive bruising and infection, evaluation of pain and/or discomfort and were given analgesics additional to the standard doses described above. Animals were euthanatized if deemed necessary by the attending veterinarian and excluded from analysis.

Daily monitoring records were kept. Unusual findings were reported to the study director and/or the veterinarian and a decision made to treat an animal or, in the case of a moribund animal, to euthanize it. Moribund animals were euthanized and recorded.

Animal husbandry personnel were blinded as to the group assignment.

Evaluation of adhesions: 15-16 days following surgery, animals were euthanized by intravenous injection of 1.5 ml of Beuthanasia-D (sodium pentobarbital 390 mg/ml; phenytoin sodium 50 mg/ml) (Merck Animal Health, Madison, N.J.). Body weights of the animals were recorded. The abdomen was opened and the surgical site inspected.

Adhesions were graded by a blinded observer.

The length of each uterine horn with adhesions was estimated. Results were expressed as incidence of adhesions (number of uterine horns with adhesions/total number) and extent of adhesions (% length of uterine horn with adhesions).

Tenacity (Severity) of Adhesions (Grade) were graded as 0 (absent), 1 (filmy adhesions), and 2 (tenacious, requiring sharp dissection).

The degree of uterine convolution, a measure of the anatomical distortion of the organ due to adhesions, was recorded according to the following scale:

No convolution: straight lengths of adherent or nonadherent horns that are clearly seen Partly convoluted: horns have adhesions and 50%-75% of the horn length is entangled preventing discernment of the straight portions Completely convoluted: it is impossible to see the uterine anatomy because the horn is completely entangled.

Tissue samples were taken into formalin for possible future histology. No histology was performed. Representative photographs were taken during surgery and evaluation.

Data were entered onto a spreadsheet by hand and transcribed into a personal computer using Microsoft Excel for Windows, with double checking. For each animal, the average % extent of adhesions was calculated for the two horns. This average was used to calculate the mean extent (percent of the length of the uterus involved) of adhesions (±SEM) for the group, displayed to one decimal place. Comparisons of all groups with the Control group were made using Dunnett's test (Dunnett CW. New tables for multiple comparisons with a control. Biometrics 20:482-491 (1964); "Dunnett, 1964"). The incidence of adhesions was compared using Fisher's Exact Test, and the tenacity and degree of uterine convolution was compared using the $\chi^2$ test. For all tests, the level of statistical significance was taken as $p<0.05$.

Results

The results for evaluation of adhesion sites are presented in Table 2 below.

TABLE 2

| | Concentration in the fibrinogen component | | | |
|---|---|---|---|---|
| Parameter | Negative Control | 2-fold dilution EVICEL ® ("#1"): Fib. 32 mg/ml Thr. 512 IU/ml | 4-fold dilution EVICEL ® ("#2"): Fib. 12 mg/ml Thr. 260 IU/ml | Seprafilm ® |
| % Adhesions* | 77.6% | 43.8% | 21.9% | 32.8% |
| Severity** | | | | |
| Absent | 0% | 8% | 16.7% | 8% |
| Filmy | 0% | 42% | 42% | 25% |
| Tenacious | 100% | 50% | 42% | 67% |
| Convolution*** | | | | |
| No | 25% | 50% | 92% | 58% |
| Partially | 50% | 42% | 8% | 25% |
| Completely | 25% | 8% | 0% | 16.7% |

| | Concentrations after mixing fibrinogen with Thrombin 1:1 | | | |
|---|---|---|---|---|
| Parameter | Negative Control | 2-fold dilution EVICEL ® ("#1"): Mixed components Fib. 16 mg/ml Thr. 206 IU/ml | 4-fold dilution Mixed components EVICEL ® ("#2"): Fib. 6 mg/ml Thr. 130 IU/ml | Seprafilm ® |
| % Adhesions* | 77.6% | 43.8% | 21.9% | 32.8% |
| Severity** | | | | |
| Absent | 0% | 8% | 16.7% | 8% |
| Filmy | 0% | 42% | 42% | 25% |
| Tenacious | 100% | 50% | 42% | 67% |
| Convolution*** | | | | |
| No | 25% | 50% | 92% | 58% |
| Partially | 50% | 42% | 8% | 25% |
| Completely | 25% | 8% | 0% | 16.7% |

TABLE 2-continued

1) *% Adhesions = % length of uterine horn with adhesions
2) **The severity is presented as the % number of uterine with the following severity grades: absent/filmy adhesions/tenacious, requiring sharp dissection
3) ***The degree of uterine convolution, a measure of the anatomical distortion of the organ due to adhesions is presented as the % number of uterine with the following convolution grades:
4) No convolution: straight lengths of adherent or nonadherent horns that are clearly seen
5) Partly convoluted: horns have adhesions and 50%-75% of the horn length is entangled preventing discernment of the straight portions
6) Completely convoluted: it is impossible to see the uterine anatomy because the horn is completely entangled.

Extensive adhesions were observed in the Control group animals (78±4.4%, N=6). A statistically significant (Dunnett's t test) reduction in the % extent of adhesion formation was observed for animals treated with either EVICEL® derived #1 (44±9.8%, N=6; p<0.05), EVICEL® derived #2 (22±7.4%, N=6; p<=0.01) or Seprafilm (33±11.6%. N=6; p<=0.01) as compared with the Control animals (no treatment).

The incidence of adhesions was 100% (12/12 horns) for the Control group, 92% (11/12 horns) for the EVICEL® derived #1 Group, 83% (10/12 horns) for the EVICEL® derived #2 group and 92% (11/12 horns) for the animals treated with Seprafilm. These differences were not statistically significant (Fisher's Exact Test).

Both EVICEL®-derived formulations showed a statistically significant reduction in the tenacity of adhesions as compared with controls (p<0.05, $\chi^2$ test), whereas the reduction in the tenacity as compared to Seprafilm was insignificant (p=0.12).

Only EVICEL® derived #2 group showed a statistically significant reduction in the degree of uterine convolution, a measure of anatomical distortion, as compared with the Control group (p=0.004, $\chi^2$ test). EVICEL®% derived #1 and Seprafilm showed a downshift in the degree of uterine convolution, but this was not statistically significant.

As can be seen from Tables 2A-2B, while the 32 mg/ml fibrinogen concentration provided an effect compared to the negative control, the lower concentration of fibrinogen of 12 mg/ml in the fibrinogen component (Table 2A), or concentration of fibrinogen of 6 mg/ml (Table 2B) after mixing with thrombin solution 1:1, provided a much greater effect, which was better than the commercially available product Seprafilm® in every respect. The total % of adhesions was lower; the adhesions were less severe with more absent adhesions and fewer tenacious adhesions; and there was only one partly convoluted adhesion (and no completely convoluted adhesions), compared to 5 convoluted adhesions (2 complete) in the Seprafilm® group.

Example 2: Effect of Fibrinogen and Albumin in a Rabbit Uterine Horn Model

The purpose of this study was to characterize the efficacy of various formulations with different concentrations of fibrinogen and albumin in a rabbit uterine horn adhesion model.

Materials and Methods:
The Test System

Juvenile/young adult (13-15 weeks old at surgery) female New Zealand white rabbits (*Oryctolagus cuniculus*) were used in the study. Rabbits were obtained from Western Oregon Rabbit Co., PO Box 653, Philomath, Oreg. USA and were individually identified by unique, ear tags, applied by the supplier.

Animals were examined by experienced animal care personnel shortly after arrival at the test facility.

Animals were acclimated for a minimum of 5 days prior to initiation of the study and monitored by experienced animal care personnel daily. Animals supplied for this study were used only if they appeared grossly normal (i.e., showing a clean unruffled coat, bright clear eyes, no unusual exudate from body orifices, alert and active posture).

Environment and Husbandry:

Animals were individually housed in stainless steel cages, each labeled with an individual card indicating the study number and the individual animal number. The room environment was maintained at approximately 68° F. (approximately 20° C.) with 30-70% relative humidity and a light/dark cycle of 12 hours/12 hours.

Purina Prolab Rabbit diet 15% protein (LabDiet, St. Louis, Mo.) and tap water was provided ad libitum to the animals for the duration of the study and carrots and alfalfa cubes.

Pre-Operative Preparation: Adhesion was studied using surgery. Animals were weighed on the day of surgery. Anesthesia was induced and maintained by inhalation of isoflurane (5% and 3.5% concentration, respectively). Depilation of the surgical site was accomplished with an electric animal clipper. The area was vacuumed to remove hair clippings and debris, and then rinsed with isopropyl alcohol 70%. The bladder was expressed (i.e. manipulated externally to force urine out of it). The entire area was painted with an aqueous iodophor solution (iodine scrub) of 1% available iodine. The area was then swabbed with 70% isopropyl alcohol solution.

Procedures were performed in a sterile manner in a room reserved for aseptic survival surgery. Sterile towels, drapes, and instruments were used. The anesthetized and surgically prepared rabbit was delivered to the operating table and restrained via the limbs in the desired recumbent position. A sterile incise drape was applied to the prepared area. Since there is an approximate correlation between animal weight and uterine horn size, in order to avoid operating on animals with smaller or larger out-of-range horns, and since there were two consecutive surgery days in each of two consecutive weeks, animals were assigned to surgery in a sequential order based on their weight. The assignment of an animal to one of the study groups was made according to its sequential surgery assignment.

Justification of the Test System:

The rabbit uterine horn simple abrasion model is performed essentially as described in Wiseman 1992 (Effect of thrombin induced hemostasis on the efficacy of an absorbable adhesion barrier. The journal of reproductive medicine vol 37 No 9, September 1992), with and without the bleeding modification.

Six animals per group are to be entered into the study. Given the variances observed historically, these group sizes are sufficient to provide the study with sufficient power to detect statistical differences between treatment and control group.

This model has been used extensively for the determination of efficacy of putative anti-adhesion agents, and good correlations exist between data obtained in animals and that obtained clinically (Wiseman, 1999 Effect of different barriers of oxidized regenerated cellulose (ORC) on cecal and sidewall adhesions in the presence and absence of bleeding. Journal of Investigative Surgery 12.141-146).

The 42 sequentially assigned animals were randomized by lottery by a disinterested individual in blocks of 7 so that each of the study groups was represented in each block.

The rabbit uterine horn simple abrasion model was conducted as described by Wiseman et al., 1992.

Intra-Operative Procedure: The abdomen was entered via a midline laparotomy incision about 6 cm long. The bladder and uterus were delivered into the wound. Only those animals with two uterine horns with a diameter of between 9 and 16 French, inclusive, were entered into the study. Using a number 10 scalpel blade, 5 cm lengths of uterine horn, approximately 1 cm from the uterine bifurcation, were scraped, 40 times per side. Hemostasis was controlled by tamponade with gauze. If necessary small vessels were ligated. Organs were repositioned anatomically. During the treatment, the animals were observed carefully to remove any animal with unexpected response to the anesthetic treatment. Controls consisted of animals in which all surgical procedures have been performed, but without the application of test materials.

Tested formulas were used in vials of 5 ml of each component per animal were thawed at room temperature before induction of anesthesia. Each product was handled according to the manufacturer's instructions and delivered by spraying using the Omrix application airless spray device. Enough product was applied so as to cover the traumatised surfaces with a thin film. The volume applied was recorded.

Post-Operative Procedure: Abdominal incisions were closed using a continuous Vicryl 4-0 suture. Fascia was closed loosely with 4-0 Vicryl and the skin closed with undyed 4-0 Vicryl (cutting needle) using a subcuticular suturing method. Three doses of buprenorphine (Buprenex) (0.03 mg/kg, 0.4 ml×0.3 mg/ml) were given by subcutaneous injection, one on the morning of surgery, one six to eight hours later and one the following morning. Further doses were given if deemed necessary by the veterinarian.

Clinical Signs of Animals: All animals were observed closely until vertical recumbence was resumed, when they were returned to their cages. Rabbits were placed under a heat lamp or on a heating blanket for this initial post-operative period.

Each rabbit was observed daily after surgery to determine its health status on the basis of general attitude and appearance, food consumption, weight loss, fecal and urinary excretion and presence of abnormal discharges. Animals were observed daily for incisional integrity, excessive bruising and infection, evaluation of pain and/or discomfort and were given analgesics additional to the standard doses described above. Animals were euthanatized if deemed necessary by the attending veterinarian and excluded from analysis.

Daily monitoring records were kept. Unusual findings were reported to the study director and/or the veterinarian and a decision made to treat an animal or, in the case of a moribund animal, to euthanize it. Moribund animals were euthanized and recorded. Animal husbandry personnel were blinded as to the group assignment.

Adhesion and Tenacity Detection: Adhesion evaluation was done 11-16 days following surgery, animals were euthanized by intravenous injection of 1.5 ml of Beuthanasia-D (sodium pentobarbital 390 mg/ml; phenytoin sodium 50 mg/ml) (Merck Animal Health, Madison, N.J.). Body weights of the animals were recorded. The abdomen was opened, and the surgical site inspected. Adhesions were graded by a blinded observer.

Examinations Performed

Extent and Incidence of Adhesions: The length of each uterine horn with adhesions is estimated. Results are expressed as incidence of adhesions (number of uterine horns with adhesions/total number) and extent of adhesions (% length of uterine horn with adhesions).

Tenacity of Adhesions: Tenacity (Severity) of Adhesions (Grade) is graded as 0 (absent), 1 (filmy adhesions), and 2 (tenacious, requiring sharp dissection). Degree of Uterine Convolution: The degree of uterine convolution, a measure of the anatomical distortion of the organ due to adhesions, is recorded according to the following scale:

No convolution: straight lengths of adherent or nonadherent horns that are clearly seen;

Partly convoluted: horns have adhesions and 50%-75% of the horn length is entangled preventing discernment of the straight portions;

Completely convoluted: it is impossible to see the uterine anatomy because the horn is completely entangled.

Data Analysis of Adhesions: For each animal, the average extent of adhesions is calculated for the two horns. This average is used to calculate the mean extent (percent of the length of the uterus involved) of adhesions (±SEM) for the group, displayed to one decimal place. Comparisons of all groups with the Control group (no treatment) are made using Dunnett's test (Dunnett, 1964). The incidence of adhesions of each group is compared with controls using Fisher's Exact Test, and the tenacity and degree of uterine convolution is compared using the chi2 test. For all tests, the level of statistical significance is taken as $p<0.05$.

Exclusion from Analysis: upon examination of an animal at necropsy, but before inspection of the surgical site and evaluation of adhesions, a determination is made as to whether the animal should be excluded from the primary analysis. Animals are to be excluded from the primary analysis if there are signs of unusual occurrences that may affect the outcome. Such signs commonly include presence of infection within the abdominal cavity, or excessive weight loss (>10% of body weight). Any decision to exclude an animal is made without knowledge of the group assignment or of the presence or extent of adhesions.

TABLE 3

BAC2 and Thrombin Albumin-based buffer solution formulas*

| Material | Reagent | Concentration |
|---|---|---|
| BAC2 buffer (With Albumin) | Sodium Chloride | 120 mM |
| | Tri-Sodium Citrate dihydrate | 10 mM |
| | Glycine | 120 mM |
| | Arginine hydrochloride | 9.5 mM |
| | Calcium chloride dihydrate | 1 mM |
| | Human albumin | 11% |
| | pH | 7.0-7.2 |
| Thrombin buffer (With Albumin) | Sodium Acetate trihydrate | 20 mM |
| | D-Mannitol | 0.1M |
| | Calcium chloride dihydrate | 40 mM |
| | Human Albumin | 0.6% |
| | Sodium Chloride | ~90 mM |
| | pH | 6.8-7.2 |

*(Thrombin and albumin surrogate)

Applicator devices for all formulations: The EVICEL® Application Device with the EVICEL® Airless Spray Accessory is used to apply the formulations according to the Assembly guide and the manufacturer instructions.

TABLE 4 with experimental details

| Exp. No. | Total protein (mg/ml) in Thr/BAC 2 1:1 | Fibrinogen (mg/ml) in Thr/BAC2 1:1 | Total albumin (mg/ml) in Thr/BAC2 1:1 | Fibrinogen % from total protein in Thr/BAC2 1:1 | Total protein (mg/ml) | Albumin (Alb) mg/ml In BAC2 (mg/ml) | Albin Thr (mg/ml) | Fibrinogen (mg/ml) | Fibrinogen component Source of fibrinogen and buffer | Thrombin component Thrombin (IU/ml) and Source of thrombin buffer |
|---|---|---|---|---|---|---|---|---|---|---|
| 1 | 45.5 | 11.5 | 42 | 25% | 91 | 77 | 6 | 23 | BAC2(1:2) W/albumin | 161 W/albumin |
| 2 | 47 | 4.5 | 50 | 9.5% | 94 | 94 | 6 | 9 | BAC2(1:6) W/albumin | 161 W/albumin |
| 3 | 18 | 11.5 | 3 | 67% | 36 | 4 | 2 | 23 | BAC2(1:2) W/O albumin | 153 W/O albumin |
| 4 | 10 | 5.5 | 1.5 | 55% | 20 | 2 | 1 | 11 | BAC2(1:6) W/O albumin | 153 W/O albumin |
| 5 | 55 | 7 | 58 | 13.7% | 102 | 110 | 6 | 14 | pure fibrinogen W/albumin | 161 W/albumin |
| 6 | 55 | 8.5 | 58 | 21.25% | 80 | 110 | 6 | 17 | pure fibrinogen W/albumin | 161 W/albumin |

TABLE 5

Results summary for the assessment of the effect of fibrin-based formulations on adhesion formation

| Representative Exp. (No.) | Average Extent (Adhesion)%[1] | p[2] | Adhesion Free[3] | Grade[4] | P# | Conv[5] | p# |
|---|---|---|---|---|---|---|---|
| control | 67 | NA | 0 | 0/1/11 |  | 3/5/4 |  |
| 1 | 32 | 0.039 | 6.3 | 1/5/10 |  | 12/4/0 | 0.012 |
| 2 | 33 | 0.047 | 0 | 0/5/7 |  | 10/2/0 | 0.012 |
| 5 | 33 | 0.07 | 7.1 | 1/6/7 | 0.078 | 8/4/2 |  |
| 6 | 59 | 0.67 | 7.1 | 1/4/9 |  | 9/1/4 | 0.063 |

[1] % of length of uterine horn with adhesions, mean of left and right horns
[2] p value for Student's t- test against Control
[3] % of uterine horns free of adhesions (number of uterine horns free of adhesions/total)
[4] Number of horns with no adhesions/grade 1 adhesions/grade 2 adhesions
[5] Number of horns with no convolution/partial convolution/full convolution
* $p < 0.05$ Dunnett's t test vs. Control
p value $\chi$ 2 test, vs Control). Only values <0.1 shown.

TABLE 6

Summary of discrete data statistic for 6-8 samples used for the anti-adhesion experiments tested for each composition (fibrinogen component)

| Threshold set to above 35% | Control | #1 (mg/ml) *FGBAC2 23 + total prot 91 + alb 77 | #2 (mg/ml) FGBAC2 9 + total prot 94 + alb aprox 94 | #5 (mg/ml) **FGPure Fibrinogen 14 + total protein 102 + alb. aprox. 110 | #6 (mg/ml) FG Pure Fibrinogen 17 + total protein 80 + alb. approx. 110 |
|---|---|---|---|---|---|
| Extent *** | 70.0 | 45.0 | 35.0 | 75.0 | 42.5 |
| Extent *** | 90.0 | 40.0 | 41.5 | 15.0 | 100.0 |
| Extent *** | 60.0 | 33.5 | 60.0 | 11.0 | 7.5 |
| Extent *** | 10.5 | 65.0 | 8.0 | 11.0 | 45.0 |
| Extent *** | 92.5 | 10.0 | 35.0 | 5.0 | 90.0 |
| Extent *** | 77.5 | 16.0 | 20.0 | 80.0 | 25.0 |
| Extent *** |  | 4.0 |  | 33.0 | 100.0 |
| Extent *** |  | 41.5 |  |  |  |
| Average Extent *** | 67 | 32 | 33 | 33 | 59 |
| individual results above the threshold | 5 | 4 | 2 | 2 | 5 |
| Overall No. of results per group | 6 | 8 | 6 | 7 | 7 |
| Proportion of results above threshold | 0.83 | 0.50 | 0.33 | 0.29 | 0.71 |

*FGBACII = fibrinogen in BACH;
**FGPure Fibrinogen = Fibrinogen in Pure fibrinogen;
*** % adhesion

TABLE 7

Summary of discrete data statistic for 6-8 samples for the anti-adhesion experiments tested for each composition (fibrinogen and thrombin)

| Threshold set to above 35% | Control | #1 (mg/ml) FGBAC2 11.5 + total prot. 45.5 + alb 42 | #2 (mg/ml) FGBAC2 4.5 + total prot. 47 + alb approx. 50 | #5 (mg/ml) FGPure fibrinogen 7 + tot. protein 54 + alb aprox. 58 | #6 (mg/ml) FGPure fibrinogen 8.5 + tot. prot 43 + alb approx. 58 |
|---|---|---|---|---|---|
| Extent* | 70.0 | 45.0 | 35.0 | 75.0 | 42.5 |
| Extent* | 90.0 | 40.0 | 41.5 | 15.0 | 100.0 |
| Extent* | 60.0 | 33.5 | 60.0 | 11.0 | 7.5 |
| Extent* | 10.5 | 65.0 | 8.0 | 11.0 | 45.0 |
| Extent* | 92.5 | 10.0 | 35.0 | 5.0 | 90.0 |
| Extent* | 77.5 | 16.0 | 20.0 | 80.0 | 25.0 |
| Extent* |  | 4.0 |  | 33.0 | 100.0 |
| Extent* |  | 41.5 |  |  |  |
| Average Extent* | 67 | 32 | 33 | 33 | 59 |
| individual results above the threshold | 5 | 4 | 2 | 2 | 5 |
| Overall No. of results per group | 6 | 8 | 6 | 7 | 7 |
| Proportion of results above threshold | 0.83 | 0.50 | 0.33 | 0.29 | 0.71 |

*% adhesion

Table 3 shows the buffers used for dilution of fibrinogen and thrombin with albumin. Table 4 shows the concentrations of albumin (calculated), fibrinogen (measured), and total protein (measured) in the fibrinogen component and in the mixture of fibrinogen and thrombin in representative samples.

A threshold was set to 35% or below as indication to efficient antiadhesion extent (Tables 6 and 7). In samples 2 and 5 the majority of the tested samples were equal to or below this threshold. The results show that a fibrinogen component comprising total protein at a concentration of 94 and 102 mg/ml and a low concentration of fibrinogen of about 9 and 14 mg/ml samples 2 and 5 respectively, can be used in a kit for efficient prevention or reduction of adhesion (Table 5 and Table 6).

It was found that a mixture of fibrinogen and thrombin comprising total protein at a concentration of 47 and 55 mg/ml and a concentration of fibrinogen of 4.5 and 7 mg/ml samples 2 and 5 respectively, can be used for efficient prevention or reduction of adhesion (Table 5 and Table 7).

It was found that a fibrinogen component comprising albumin at a concentration of 94 and 110 mg/ml and a low concentration of fibrinogen of 9 and 14 mg/ml, samples 2 and 5 respectively, can be used in a kit for efficient prevention or reduction of adhesion (Table 5 and Table 6).

It was found that a mixture of fibrinogen and thrombin comprising albumin at a concentration 50 and 58 mg/ml and a low concentration of fibrinogen of 4.5 and 7 mg/ml; samples 2 and 5 respectively, can be used for efficient prevention or reduction of adhesion (Table 5 and Table 7).

Example 3: Impact of the Formulations on the Water Retention Under Ambient Conditions Further exemplary procedures were aimed at quantitating the % of water retention in the clots with the different formulations after 1-2 hours hydrogels formation and under ambient conditions.

Formulations 1-12 are as described in Table 8.

In formulations 9-12 "TH04" is an in-process fraction in the thrombin manufacture in which thrombin source is devoid of albumin and calcium.

After one and up to two hours following hydrogel formation (formation of hydrogel is determined by a visual inspection) under ambient conditions the hydrogel was subjected to a mild centrifugation of 630 g, having a surface area of about 1 cm$^2$ for 30 min inside a centricon tube and the amount of retained water in the hydrogel was assessed.

The results summarized in Table 8 show that the water retention capacity of the different clots is 37.4%-61.6%

Example 4: Impact of the Formulations on the Water Retention Under High Pressure Further exemplary procedures were aimed at quantitating the % of water retention in the clots with the different formulations upon centrifugation (in an Eppendorf tube 0.7-1 cm$^2$ at 31,514 g for 30 mins.), shortly after hydrogel formation (formation of hydrogel is determined by a visual inspection) under ambient conditions.

Formulations 1-12 are as described in Table 8.

The Results are summarized in Table 9 below.

TABLE 8

Impact of the formulations on the water retention under ambient conditions

| Formulation# | Fibrinogen component | | Thrombin component | | % water retained |
| --- | --- | --- | --- | --- | --- |
| | Material | Diluent | Material | Diluent | |
| 1 | BAC2 (1:4) | With albumin | Thrombin (1:4) | With albumin | With Calcium | 56.11 |
| 2 | BAC2 (1:8) | With albumin | Thrombin (1:4) | With albumin | With Calcium | 37.40 |
| 3 | BAC2 (1:4) | W/O albumin | Thrombin (1:4) | W/O albumin | With Calcium | 58.05 |
| 4 | BAC2 (1:8) | W/O albumin | Thrombin (1:4) | W/O albumin | With Calcium | 48.33 |
| 5 | BAC2 (1:4) | With albumin | Thrombin (1:4) | With albumin | W/O calcium, 5 mM EDTA | 54.15 |
| 6 | BAC2 (1:8) | With albumin | Thrombin (1:4) | With albumin | W/O calcium, 5 mM EDTA | 45.38 |
| 7 | BAC2 (1:4) | W/O albumin | Thrombin (1:4) | W/O albumin | W/O calcium, 5 mM EDTA | 42.52 |
| 8 | BAC2 (1:8) | W/O albumin | Thrombin (1:4) | W/O albumin | W/O calcium, 5 mM EDTA | 37.65 |
| 9 | BAC2 (1:4) | With albumin | TH04 100-300 IU/ml | W/O albumin | W/O calcium, 5 mM EDTA | 61.59 |
| 10 | BAC2 (1:8) | With albumin | TH04 100-300 IU/ml | W/O albumin | W/O calcium, 5 mM EDTA | 47.58 |
| 11 | BAC2 (1:4) | W/O albumin | TH04 100-300 IU/ml | W/O albumin | W/O calcium, 5 mM EDTA | 59.99 |
| 12 | BAC2 (1:8) | W/O albumin | TH04 100-300 IU/ml | W/O albumin | W/O calcium, 5 mM EDTA | 52.18 |

TABLE 9

Impact of the formulations on the water retention under high pressure

| Exp. No. | Dilution of fibrinogen | Albumin conc in the total solution mg/ml | free calcium ions are present | % retained from initial weight after 1st centrifugation | % lost from initial weight after 1st centrifugation |
|---|---|---|---|---|---|
| 1 | 1:4 | 48.20 | + | 57.55 | 42.45 |
| 2 | 1:8 | 52.20 | + | 29.32 | 70.68 |
| 3 | 1:4 | 1.8 | + | 89.66 | 10.34 |
| 4 | 1:8 | 1.25 | + | 88.52 | 11.48 |
| 5 | 1:4 | 48.20 | − | 64.35 | 35.65 |
| 6 | 1:8 | 52.50 | − | 23.55 | 76.45 |
| 7 | 1:4 | 1.80 | − | 91.19 | 8.81 |
| 8 | 1:8 | 1.25 | − | 87.97 | 12.03 |
| 9 | 1:4 | 45.20 | − | 26.87 | 73.13 |
| 10 | 1:8 | 49.50 | − | 6.92 | 93.08 |
| 11 | 1:4 | 1.20 | − | 70.46 | 29.54 |
| 12 | 1:8 | 0.67 | − | 16.89 | 83.11 |

When albumin is present at high concentration (45-52 mg/ml) or when the total protein is high e.g. of about 50 mg/ml (or 35 to 60 mg/mi), at a fibrinogen dilution of 1:4 (in Exp 1, and 5) water retention is about 50%. When albumin is present at high concentration (45-52 mg/ml) or when the total protein is about 50 mg/ml (or 35 to 60 mg/ml), and fibrinogen dilution is of 1:8 (Experiment 2, 6 and 10) water retention decreases to about 29% to about 7% of the initial weight. Complete depletion of calcium (thrombin used TH04 completely lacks calcium and EDTA was added as in Examples 9 and 10) water retention decreases. Water retention is minimal under conditions of fibrinogen dilution is 1:8 (70 mg/ml:9=7.7 mg/ml) and complete depletion of calcium ions (Table 9 sample 10).

The results also show that the clots (with fibrinogen diluted both 1:4 and 1:8) enable to retain the highest amount of water (88.5% and 90%) when albumin concentration or total protein is low (Group 4 vs. Group 2 or Group 3 vs. Group 1).

The results also show that the presence of EDTA (or absence of free calcium) did not change the clot capability to retain the water when albumin concentration or total protein is low, i.e. the trend of the water loss was the same like in Groups 1-4 (with the presence of free calcium).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A two-component composition for adhesion prevention comprising:
  component A comprising a fibrinogen solution comprising fibrinogen at a concentration of about 5 to 25 mg/ml; albumin at a concentration ranging from 60 to 110 mg/ml, and comprising free calcium ions at a concentration ranging from 0.1 μM to 1 mM; and
  component B comprising a thrombin component.

2. The two-component composition of claim 1, wherein said thrombin component comprises free calcium ions, optionally at a concentration ranging from 35 to 45 mM.

3. The two-component composition claim 1, wherein said thrombin component is devoid of a chelating agent.

4. The two-component composition of claim 1, wherein said fibrinogen in said component A is present at a concentration of 10 to 20 mg/ml.

5. The two-component composition of claim 1, wherein the component B is in the form of a liquid solution.

* * * * *